United States Patent [19]
Tetteroo et al.

[11] Patent Number: 6,022,744
[45] Date of Patent: Feb. 8, 2000

[54] METHOD FOR THE PRODUCTION OF DESICCATION TOLERANT PLANT EMBRYOIDS AND METHODS FOR GERMINATION OF DESICCATION TOLERANT EMBRYOIDS

[75] Inventors: Franciscus Abraham A. Tetteroo; Folkert Anne Hoekstra; Robert Jean Legro, all of Enhuizen, Netherlands

[73] Assignee: Incotec International B.V., Enkhuizen, Netherlands

[21] Appl. No.: 08/669,303

[22] PCT Filed: Jan. 13, 1995

[86] PCT No.: PCT/NL95/00018

§ 371 Date: Oct. 7, 1996

§ 102(e) Date: Oct. 7, 1996

[87] PCT Pub. No.: WO95/19102

PCT Pub. Date: Jul. 20, 1995

[30] Foreign Application Priority Data

Jan. 13, 1994 [EP] European Pat. Off. .............. 94200076

[51] Int. Cl.$^7$ ....................................................... C12N 5/00
[52] U.S. Cl. ............................................. 435/410; 435/431
[58] Field of Search ..................................... 435/410, 431

[56] References Cited

FOREIGN PATENT DOCUMENTS

0300730 A1  1/1989  European Pat. Off. .

*Primary Examiner*—Leon B. Lankford, Jr.
*Attorney, Agent, or Firm*—Welsh & Katz, Ltd.

[57] ABSTRACT

A method for the induction of desiccation tolerance in plant embryoids is disclosed. The method entails using an excess of absissic acid and a coating of apolar and polar hygroscopic material.

22 Claims, 18 Drawing Sheets

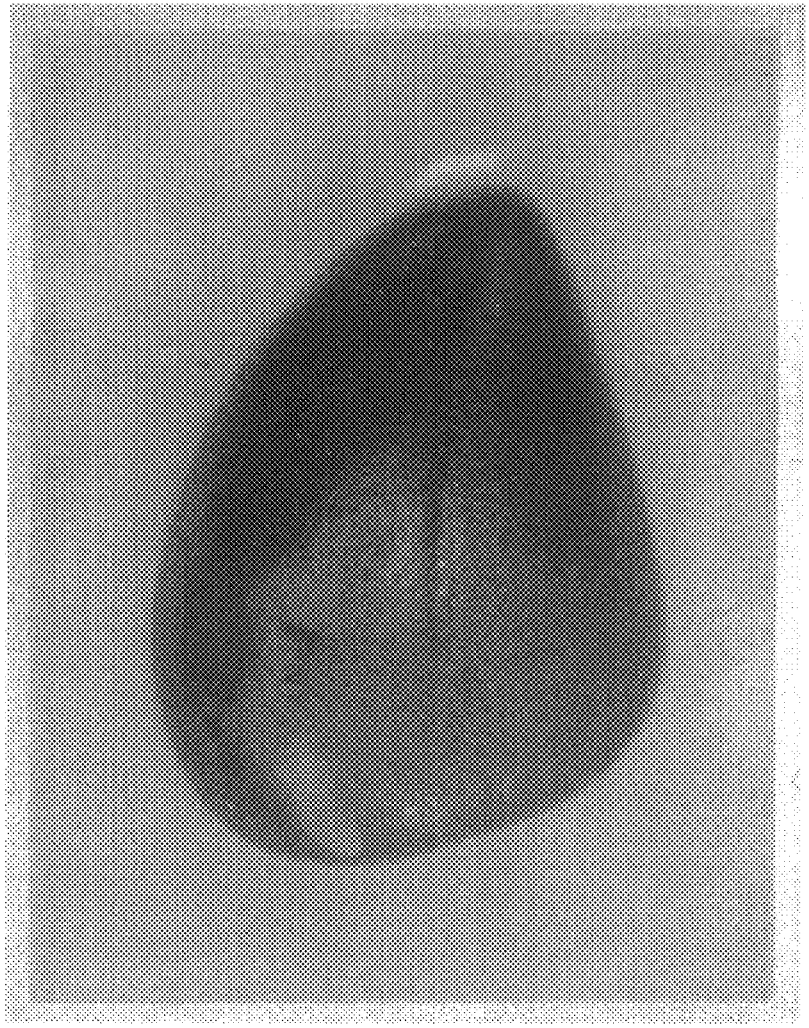
FIG. 12 - PHOTO 1

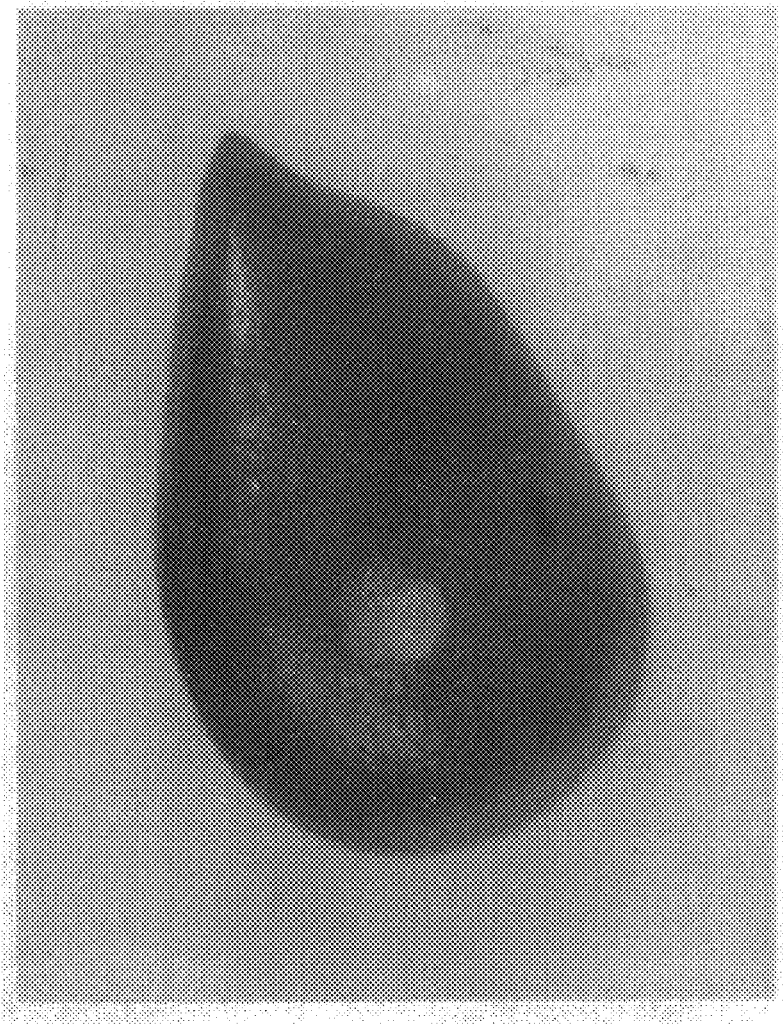
FIG. 12 - PHOTO 2

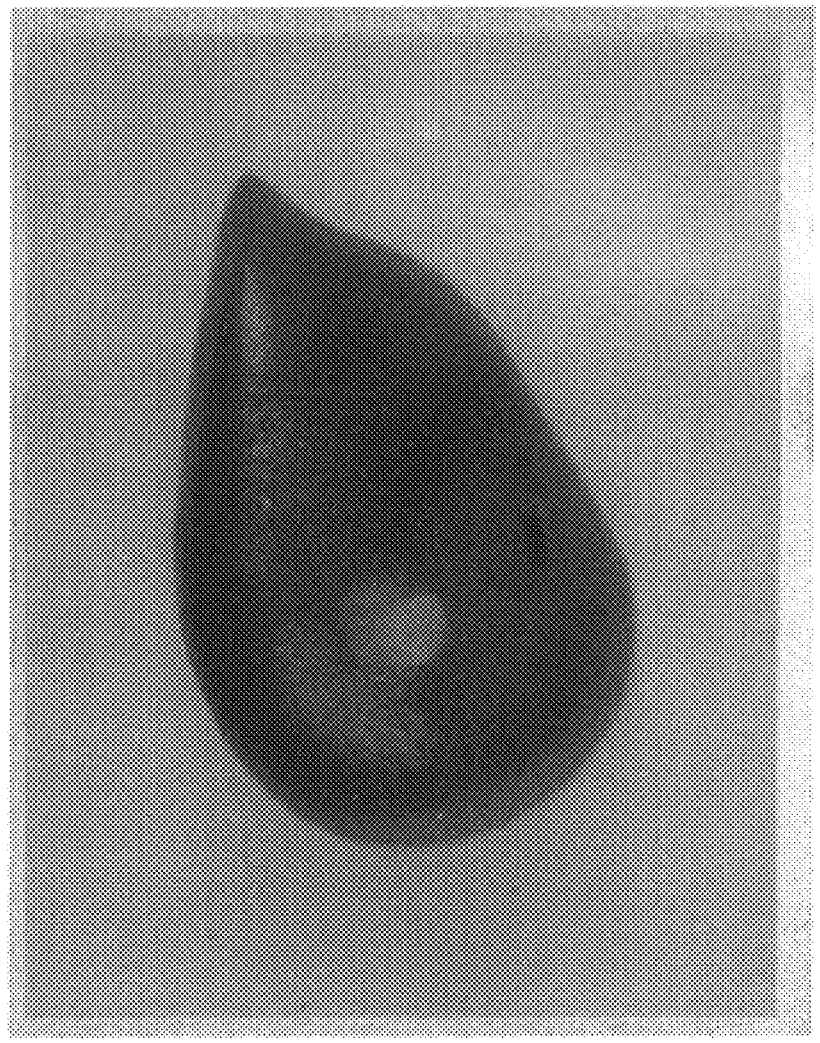
FIG. 12 - PHOTO 3

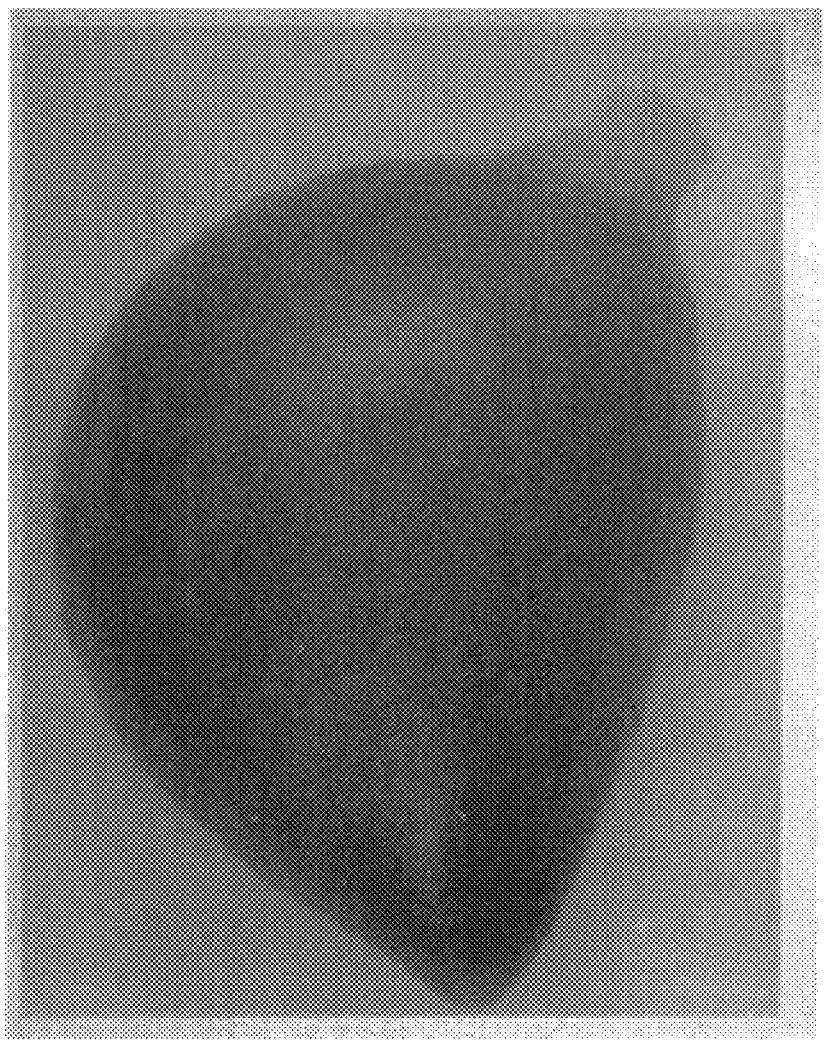
FIG. 12 - PHOTO 4

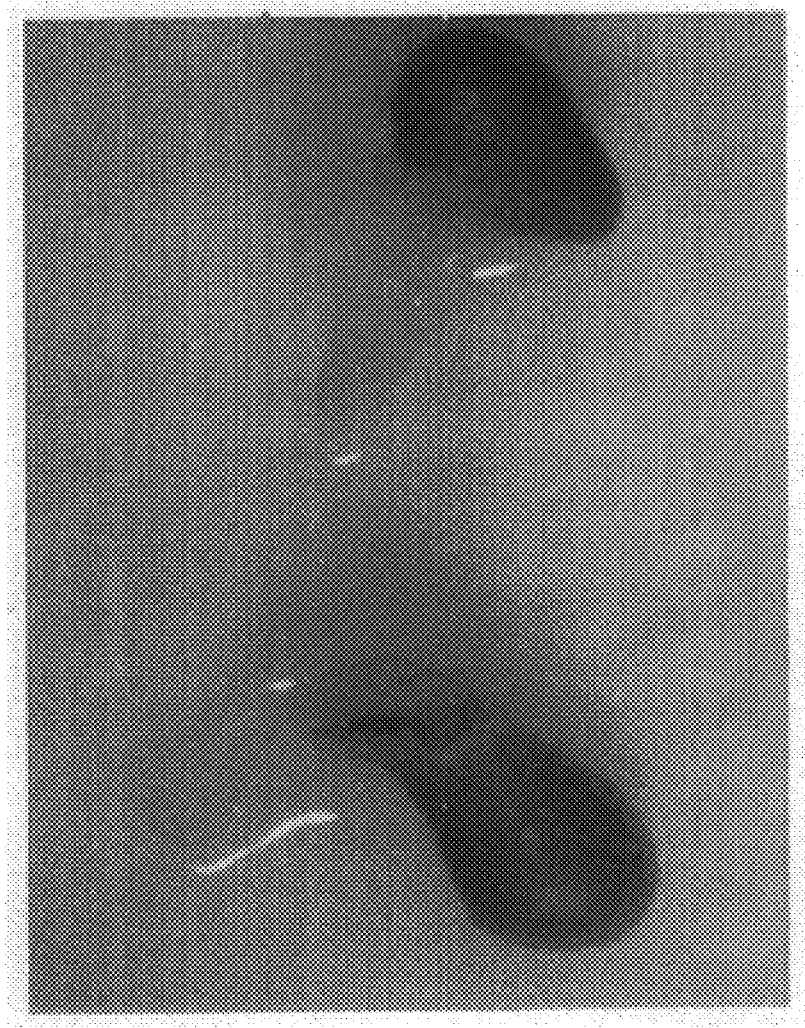
FIG. 12 - PHOTO 5

FIG. 12 - PHOTO 6

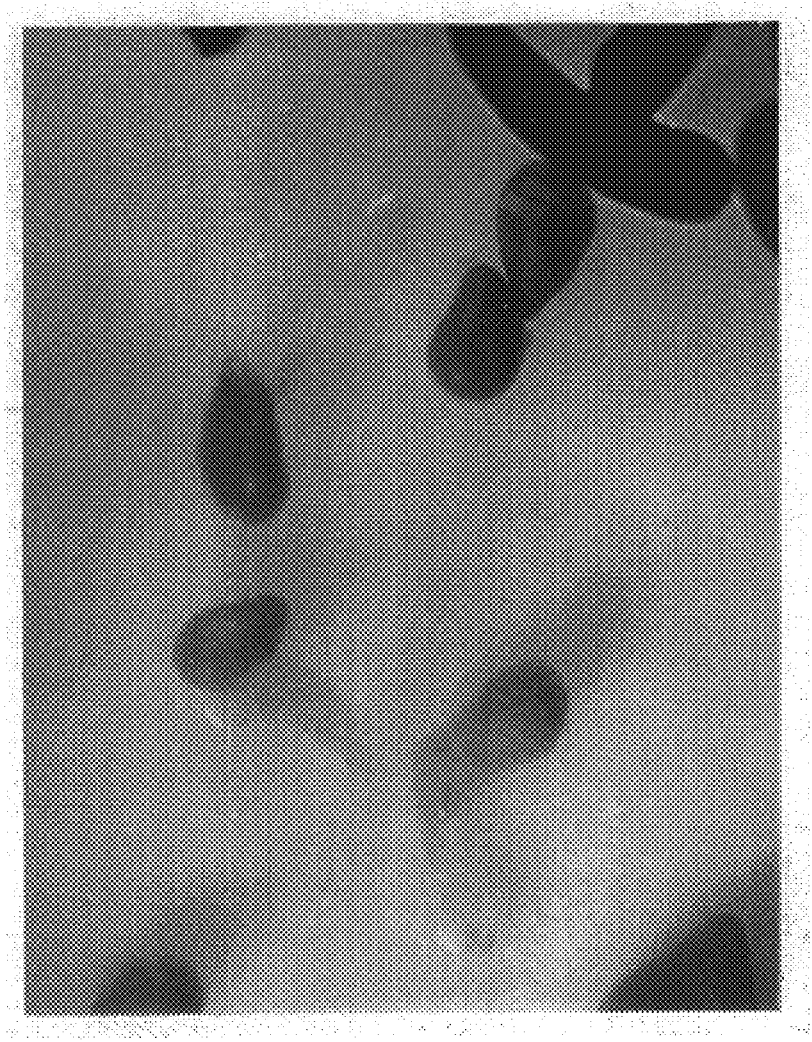
FIG. 12 - PHOTO 7

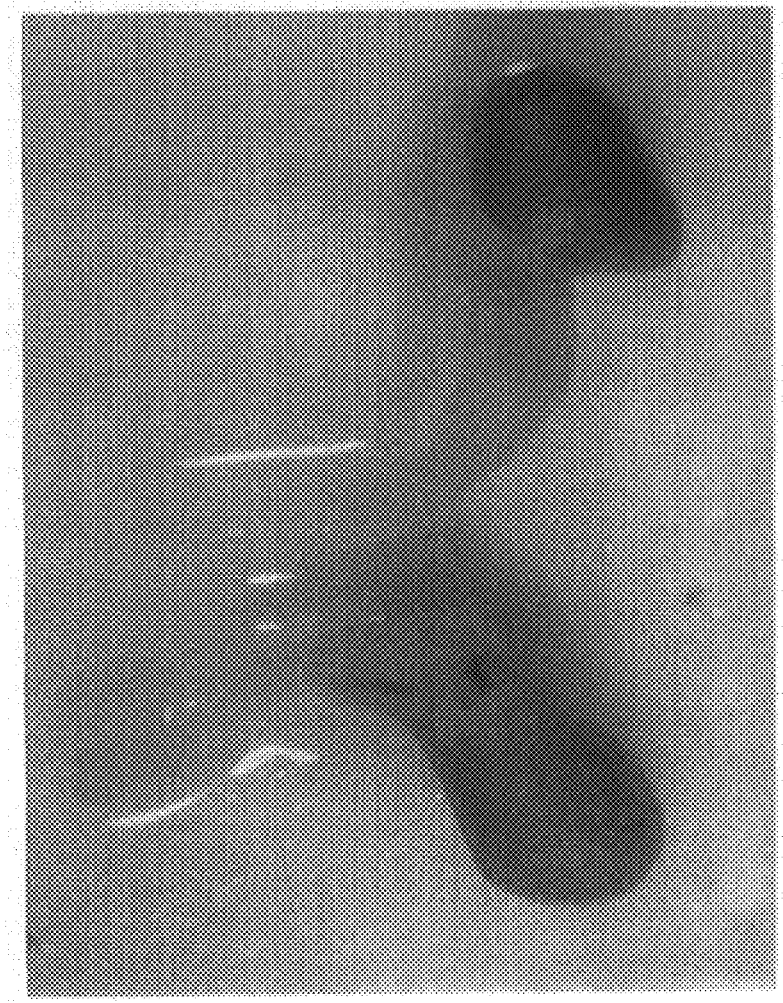
FIG. 12 - PHOTO 8

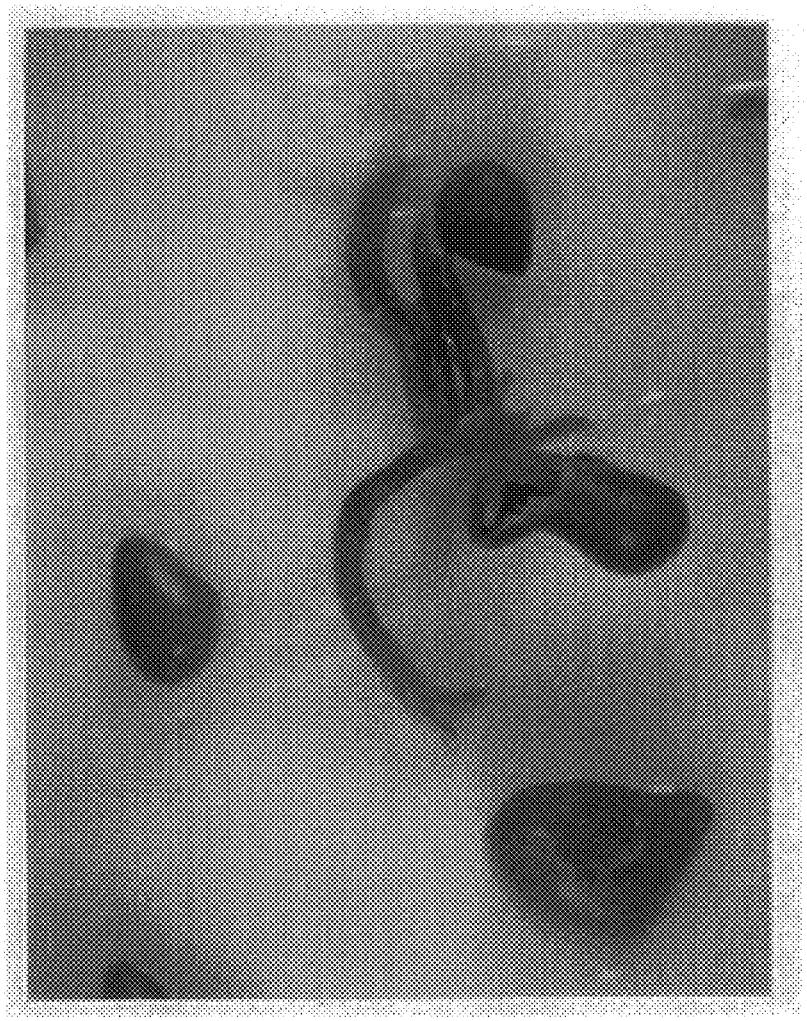
FIG. 12 - PHOTO 9

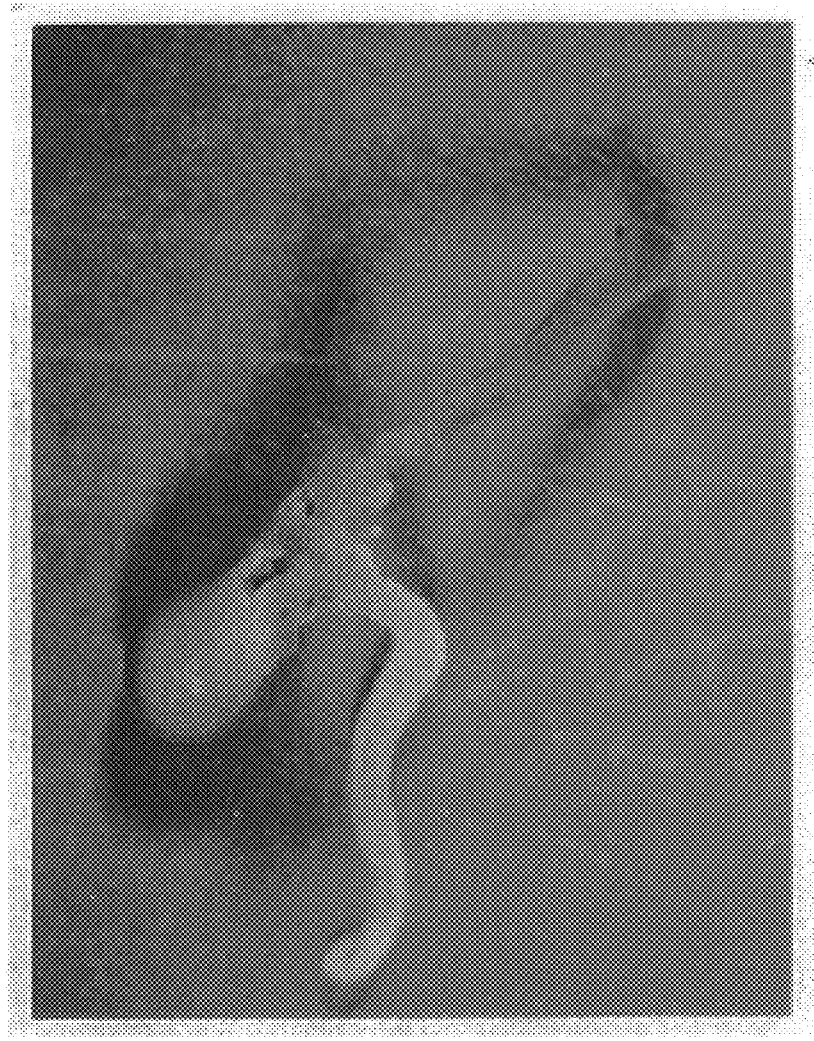
FIG. 12 - PHOTO 10

METHOD FOR THE PRODUCTION OF DESICCATION TOLERANT PLANT EMBRYOIDS AND METHODS FOR GERMINATION OF DESICCATION TOLERANT EMBRYOIDS

The invention relates to methods for the induction of desiccation tolerance in plant embryoids. It also relates to methods for the germination of embryoids which have been dessicated. Novel desiccated embryoids are also provided.

Regeneration of storable embryoids has been described for a large number of species. Redenbaugh et al. (1986) were the first to create artificial seeds by encapsulation of embryoids in alginate gel beads. However, the still hydrated artificial seeds were difficult to store, because they lacked quiescence, and the conversion rate (outgrowth into plantlets) was very low. The recent achievement of induction of tolerance to complete desiccation (Senaratna et al., 1989a) may give new opportunities to the artificial seed technology. Desiccated embryoids are better suited for use in this technology, because they are in a quiescent state comparable to that of dry seeds and they therefore have better storage properties. Gray (1990) even stated that dried grape embryoids germinated better than fresh ones.

Desiccation tolerance is defined by us as the ability of embryoids to regrow after storage at 25° C. for two weeks under low moisture conditions (e.g. 10%, comparable to dry seeds).

Production of desiccation tolerant embryoids has been published for the following species: alfalfa (Anandarajah and McKersie, 1990 and 1991; Senaratna et al., 1989a,b; McKersie et al., 1989), geranium (Marsolais et al., 1991), soybean (Parrott et al., 1988), spruce (Roberts et al., 1990; Attree et al., 1991), grape (Gray, 1990) and carrot (Lecouteux et al., 1992; Iida et al., 1992). In most studies the plant hormone abscisic acid (ABA) was used in amounts equivalent to the amounts used for inducing quiescence to induce desiccation tolerance. By adding the appropriate amounts of ABA to the culture medium at the right stage of development, depending on species and genotype, embryoids could be dehydrated to moisture contents of less than 10% (on a dry weight basis) with retention of some viability. Through the addition of ABA, it was even possible to induce desiccation tolerance in callus cultures of carrot (Nitzsche, 1980) and *Craterostigma plantagineum* (Bartels et al., 1990). Koornneef et al. (1989) and Meurs et al. (1992) have unequivocally demonstrated the role of endogenous ABA during seed development by using recombinants of ABA deficient and ABA insensitive mutants of *Arabidopsis thaliana*.

Not only exogenously supplied ABA, but also several stress treatments can induce the capacity to survive dehydration (Anandarajah and McKersie, 1990 and 1991). However, stress treatments such as heat or osmotic shock through high sucrose concentrations, may raise the endogenous ABA levels (Skriver and Mundy, 1990) and might thus induce desiccation tolerance.

The capacity of the embryoids to survive dehydration is also dependent on the drying method. Only Senaratna et al. (1989) gave a well defined description of the drying method, including drying rates and final moisture content in alfalfa embryoids.

Hoekstra et al. (1989) showed that regrowth of initially viable, dry organisms is impaired because of imbibitional damage. In all the previous studies on induction of desiccation tolerance in embryoids the plant recovery rates were always less than 100%. Poor embryoid quality, caused by less then optimal protocols, or asynchronic embryoid development could be the reason for the low recoveries.

The problem therefore remains to provide desiccated storable plant embryoids which are essentially 100% capable of germination after prolonged storage.

The invention provides such embryoids.

Also a method for germination of such embryoids in a manner that essentially all the embryoids germinate is provided.

The invention provides this solution through a method for the induction of essentially complete desiccation tolerance in plant embryoids wherein the embryoids are treated with an amount of abscisic acid activity which is significantly above the amount used to induce quiescence.

The physiological function ascribed to abscisic acid is the induction of quiescence. It has now been found that treatment of plant embryoids, especially in the torpedo stage, with a significantly higher amount of abscisic acid activity, will induce an essentially complete desiccation tolerance. To induce completely desiccation tolerant embryoids to germinate for 100%, this treatment has also proven very advantageous.

The abscisic acid activity can be provided by exogenously administered abscisic acid, but the activity can also (partly) be provided in situ. Methods to induce the production of abscisic acid in situ include, but are not limited to, temperature treatments, meaning heat shock (exposure to temperatures of 30–50° C.) and cold shock (0–10° C.), osmotic stress (exposure within the range of −0.5 to −2.5 mPa) using different salts, carbohydrates or polymers such as polyethylene glycol.

Suitable quantities of abscisic acid activity expressed in amounts of abscisic acid are from approximately 110% of the amount needed to induce quiescence to approximately 1000%, preferable from about 110–500%, most prefereable from about 120–200%, of the amount needed to induce quiescence. For carrots the amount to induce quiescence is about 3.8 $\mu$M.

Instead of in situ induction of part of the abscisic acid activity or applying exogenous abscisic acid, it is of course possible to use abscisic acid analogs such as those described in Walton ("Abscisic acid: F. A.Addicott ed., academic press, 1983, chapter 4). These analogs may be active themselves, but it is also possible that they are metabolized to abscisic acid.

The methods for induction of desiccation tolerance are most preferably applied to embryoids which are in the so called torpedo stage. Although not impossible, the induction of desiccation tolerance at other stages is much less efficient. For carrots the torpedo stage seems essential. In order to succeed in an essentially 100% germination of desiccation tolerant embryoids, it is preferred that the embryoids are prehydrated before imbibition. This prehydration prevents the damage which may result from a too rapid uptake of water. A suitable prehydration can be provided by exposing the plant embryoids to moist air with a relative humidity of 100% for at least 2 hours at 25° C. Preferably at this temperature, the treatment should not be longer then about 8 hours, because that will result in loss of viability due to a variety of reasons, for instance phase transition of the membranes. At lower temperatures the prehydration treatment may be longer.

An alternative to the prehydration step is imbibing the embryoids at a temperature above the transition temperature (Tm) of the phospholipid membranes of the embryoids (25–50° C.). Tm is the temperature at which transition takes place of membrane phospholipids from the gel phase to the liquid crystalline phase and vice versa. Another possibility is to envelop the embryoids in a coating that is capable to regulate water flow, e.g. an apolar artificial coating such as paraffin. The coating should, besides being at least partially permeable for water, be permeable for oxygen and, of course, non-toxic. We have developed suitable coatings for embryoids produced according to the invention, which coatings enable the production of storable artificial seeds, which are capable of germination for essentially 100%. The coating methods and materials as well as the coated embryoids are also part of the invention. To ensure that the embryoids rehydrate slowly when imbibed, the coatings must have some, be it minor, water permeability. Suitable coatings therefor comprise apolar, preferably wax-like materials, such as paraffin or stearin and the like. In order to provide the water permeability a more polar material has to be mixed with the wax-like material. Preferably this is a hygroscopic (inorganic) material such as clays or pumice, although other materials such as cellulose (derivatives) may be used.

Phase transition of the membranes can also be prevented by the use of trisaccharides such as trehalose, sucrose or umbelliferose, possibly as part of the coating.

Also important for a desiccation protocol which results in the invented embryoids, is the dehydration rate. When the dehydration rate is too high, this will result in embryoids uncapable of germination, because of damage to the membranes (segregation or other unwanted events may occur).

When the dehydration rate is too low the embryoids may turn brown and die before they are competely dry.

Suitable drying rates depend on the species of the embryoids, but generally speaking will be between 0.01 g $H_2O$/g dry weight per hour and 1 g $H_2O$/g dry weight per hour, preferably between 0.01 and 0.5 g $H_2O$/g, most preferably between 0.01 and 0.1 g $H_2O$/g dry weight per hour. For carrots the optimum drying rate is about 0.03 g $H_2O$/g dry weight per hour. A person skilled in the art will be able to arrive at suitable drying rates for other species. Other species that will be usable in the methods and will lead to products according to the invention are known to the person skilled in the art. They include, but are not limited to, cucumber, melon, celery, pelargonium, beans, peas, alfalfa, etc.

The invention will be illustrated in more detail in the following experimental part.

MATERIAL AND METHODS

Plant Material

Two *Daucus carota L*. genotypes were used with entirely different genetic backgrounds. One is a commercial variety cv "Trophy" and the other a breeding line "RS 1". Seeds and cell suspension cultures of cv "Trophy" were kindly provided by Dr S. de Vries of the Department of Molecular Biology, Agricultural University Wageningen. Seeds of "RS 1" were obtained from Royal Sluis, Enkhuizen, The Netherlands.

Media Preparation and Culture Conditions

All culture media were based on the Gamborg's B5 basal composition (Gamborg, 1968). Before autoclaving, the pH was adjusted to 5.8. The media were sterilized for 20 minutes at 121° C. However, ABA was dissolved in 0.2% NaHCO$_3$ and filter-sterilized (0.2 μm pore size disposable filter) before addition to the cooled medium. The cultures were grown in a climate chamber with a 16 h/day photoperiod and continuous temperature of 25° C.

Suspension Culture

After surface sterilization with 2% NaOCl (20% commercial bleach solution), the seeds were germinated on solid B5 medium (8 g/l agar). Sterile hypocotyl explants of ten day old seedlings were used to produce viable callus on solid B5 medium supplemented with 2.3 μM 2,4-D and 20 g/l sucrose (later referred to as 2,4-D-B5). Cell suspension cultures were started with 1 g callus per 50 ml 2,4-D-B5 medium in 250 ml Erlenmeyer flasks on a rotary shaker at 100 rpm. The suspensions were maintained by subculturing 2 ml PCV (packed cell volume) in 50 ml fresh medium, every 14 days. Seven days after refreshing, the cell suspensions were used to regenerate embryoids.

Embryoid Production

Regeneration of embryoids occurred after transfer of the proembryogenic masses (PEMS) to 2,4-D-free B5 medium with 20 g/l sucrose (OB5) at low density (approximately 30,000 cells/ml) (De Vries et al., 1988). In order to synchronize the embryoid development, only the PEM fraction of the cell suspension with the size between 50 μm and 125 μm diameter was used. This fraction was collected by using nylon sieves. When the PEMs had grown for seven days on OB5, the medium was refreshed to prevent exhaustion of the nutrients and to eliminate single cells that did not develop into embryoids. Also in this stage of development different amounts of ABA and sucrose were supplemented to the suspension. The refreshing of the ABA-containing medium was repeated after another seven days. The embryoids (torpedo stage) were harvested after a culture period of 18 to 20 days on a 500 μm nylon sieve.

Desiccation and Germination

Before desiccation the embryoids were thoroughly rinsed with OB5 medium in a Buchner-funnel with applied vacuum. Approximately 1 g of the freshly harvested embryoids was transferred to a sterile plastic Petri dish (9 cm) by forceps. The embryoids were equally spread out over the surface of the Petri dish. The Petri dishes were covered and placed in hygrostats (Weges, 1987). Drying rates were varied by exposure to different relative humidities (RH) inside the hygrostat at 25° C., generated by different saturated salt solutions with their RH between brackets: Na$_2$CO$_3$ (90%), NaCl (73% ), Ca(NO$_3$)$_2$ (50% ), CaCl$_2$ (30%) and LiCl (13%). Embryoids remained in the hygrostat until their moisture content was in equilibrium with the RH as measured by their weight loss. Rapid drying was effected by placing the Petri dishes without cover in the air flow cabinet. The dry weight of the embryoids was determined after freeze drying for 24 h. The moisture content was calculated as g H$_2$O/g dry weight (DW).

The viability (desiccation tolerance) of the embryoids was evaluated with a germination test. Approximately 100 dry embryoids were placed on filter paper in a sterile plastic Petri dish (6 cm). Before imbibition, the embryoids inside the closed Petri dish were prehumidified in moisture saturated air for four hours to prevent possible imbibitional damage (Hoekstra et al., 1989). Following this treatment, 1 ml OB5 medium was provided to the embryoids. The Petri dish was sealed with Parafilm and placed in an incubator with a 16 h/day photoperiod at 25° C. Embryoids were recorded as desiccation tolerant when they showed clear root growth within ten days.

Mode of Dehydration

In an attempt to regulate the drying rate in a repeatable manner, the embryoids were dried at different constant RHs (FIG. I). Rapidly dried embryoids were not able to germinate, whereas the embryoids, dehydrated slowly over a saturated Na$_2$CO$_3$ solution turned brown and died before they reached their equilibrium moisture content. Maximum survival, 49% germination, was achieved when the embryoids were dried above a saturated CaCl$_2$ solution. The different drying treatments not only varied in drying rate but also in final moisture content. In order to optimize the results, the embryoids were exposed to a range of RHs that was decreased each fourth day. This method was based on Senaratna et al. (1989a) with slight modifications. Due to a suboptimal ABA concentration (3.8 $\mu$M) during the maturation phase, the germination could only be increased with this method to maximally 76% (FIG. I).

In order to characterize the drying process, the moisture content of embryoids grown under optimal maturation conditions, 37.9 $\mu$M ABA and 60 g/l sucrose, was measured. Most of the water was lost in the first four days, but it took seven to nine days before they reached the equilibrium moisture content of 0.05 g $H_2O$/g DW. To determine the desiccation tolerance in the course of slow drying, the embryoids were quickly dehydrated to a moisture content of 0.05 g $H_2O$/g DW, at intervals. Germination increased to 100% on account of a slow drying treatment of at least four days (FIG. 1).

Imbibition and Germination

To prevent imbibitional damage by too rapid a water uptake embryoids were treated in a water vapour saturated atmosphere for different lengths of time. FIG. 2 shows that germination improved with increasing prehydration time up to eight hours, after which germination decreased. As the embryoids lack endosperm, they might need additional nutrition for proper regrowth. In Table II embryoids were germinated on B5 medium or water. Without the nutrition, the embryoids germinated very poorly (4–5%), while with B5 medium the regrowth was optimal (98%). Potassium leakage measurements revealed that embryoids imbibed in water with a four hour prehydration treatment leaked at a considerably higher rate than those imbibed in B5 medium (data not shown).

Embryoid Maturation

Osmotic stress and ABA are the main parameters that play a role in the embryoid maturation. Therefore, concentrations of sucrose and ABA in the maturation medium were varied. ABA was supplemented to the medium one week after the start of the embryoid development. Earlier addition of ABA hindered embryoid development whereas too late an addition did not prevent precocious germination (data not shown). The concentration of added ABA had a clear effect on desiccation tolerance. Germination reached its maximum between 19 and 37.9 $\mu$M ABA (FIG. 3). At higher ABA concentrations desiccation tolerance was still high, but the yield of torpedo-shaped embryoids decreased due to an impediment of development at earlier stages. At lower ABA concentrations desiccation tolerance decreased. After imbibition only the roots elongated, while the hypocotyls and cotyledons turned brown.

The amount of reserves was estimated by measurements of the dry matter content. Embryoids grown without ABA had a much lower percentage dry weight than those grown with ABA addition, because they were already germinating and had elongated roots and hypocotyls. Elevated ABA concentrations hardly further increased the accumulation of dry matter (FIG. 4). The sucrose concentration had no effect on desiccation tolerance at the optimal ABA concentration of 37.9 $\mu$M, particularly not in genotype "Trophy" (Table III). But at 3.8 $\mu$M ABA high sucrose concentrations (osmotic stress) had a positive effect on the germination. Elevated sucrose levels increased the dry matter content of the embryoids (FIGS. 4 and 5). However, the higher sucrose concentrations impeded embryoid development similarly as the elevated ABA concentrations, and the number of embryoids was reduced. The optimal sucrose concentration of the maturation medium for embryoid yield and regrowth performance was 60 g/l for "Trophy" and 20 g/l for "RS 1" (data not shown).

Embryoid Development

Through subculturing at low density in 2,4-D-free B5 medium, PEMs develop into the subsequent embryogenic stages: globular, heart and torpedo shape. The transition from undifferentiated to differentiated growth is coincided with a decrease of moisture content (FIG. 6). The "RS 1" embryoids reached the torpedo stage after 10 days. The torpedo shaped embryoids have a moisture content of approximately 6 g $H_2O$/g DW. Without ABA the embryoids then started to germinate precociously, which caused an increase in moisture content. When ABA (37.9 $\mu$M) was added the torpedo embryoids continued their development, while their moisture content dropped to 3 to 4 g $H_2O$/g DW. The decrease of the moisture content after 20 days of the ABA treated embryoids is due to the drying treatment over the saturated salt solutions. As a comparison the moisture content of carrot seeds during their development is also shown in FIG. 6.

Exposure of torpedo embryoids for three days to ABA was sufficient to induce desiccation tolerance for genotypes "RS 1" and "Trophy" (FIGS. 7 and 8). The germination percentage increased within this period for both genotypes to 100%. Globular- and heart-shaped embryoids, younger then 10 days, never showed regrowth. Without ABA maximally 20% of the "RS 1" embryoids and 45% of the "Trophy" embryoids germinated after a slow dehydration to 0.05 g $H_2O$/g DW moisture content. Exogenous ABA seems not to be the crucial factor, but it enhances the desiccation tolerance significantly. When the "Trophy" embryoids were cultured for more then 11 days on ABA containing media the capacity to survive dehydration decreased, probably because they were producing secondary embryoids on their axes.

During production of desiccation tolerant carrot embryoids we distinguish four subsequent phases; embryoid development, maturation, dehydration and germination. It is demonstrated in the present description that 100% germination of rehydrated embryoids can only be reached when the importance of these four phases is recognized. Iida et al. (1992) reached 75% germination because they only optimized the maturation phase by varying the ABA treatment. Lecouteux et al. (1992) also claimed complete desiccation tolerance in carrot embryoids, with retention of viability for up to eight months at 4° C. However, their embryoids still had a moisture content of 0.35 g $H_2O$/g DW (25%) during the quiescent phase, which is far more than the usual moisture content of seeds in storage (e.g. dry carrot seeds, 10% ). According to our definition, these embryoids can not be called "desiccation tolerant". The embryoids might have been able to survive the storage period of eight months, because of partial dehydration at low temperature, under conditions of which metabolism is much reduced.

Desiccation tolerance of embryoids has been reported also for other plant species, but the methods described so far fail to attain 100% regrowth of the dried specimen (Anandarajah and McKersie, 1990 and 1991; Senaratna et al., 1989a,b; McKersie et al., 1989; Marsolais et al., 1991; Parrott et al., 1988; Roberts et al., 1990; Attree et al., 1991; Gray, 1990). The authors did not pay full attention to the four subsequent phases in the embryoid production, which are discussed in more detail hereafter.

Embryoid Development

For carrots it seems that only torpedo shaped embryoids, formed 7–10 days after the start of the culture, are able to tolerate the drying treatment (FIGS. 7 and 8 ). The preceding embryogenic stages, globular- and heart shaped, were never desiccation tolerant. In a similar way barley embryos acquired desiccation tolerance at a certain developmental stage (16 days after pollination) and Arabidopsis embryos 12 days after pollination (Bartels et al., 1988; Koornneef et al., 1989). Senaratna et al. (1989a and b) demonstrated with alfalfa that only torpedo and cotyledonary embryoids were able to germinate after desiccation. Iida et al. (1992) obtained with carrot similar results and suggested that only the torpedo embryoids were responsive to ABA. These data support the idea that somatic embryogenesis mimics zygotic embryogenesis.

Maturation

As soon as the histodifferentiation was completed the embryoids started to mature. The maturation phase is characterized by the deposition of lipids, proteins and carbohydrates (reserves) (Kermode, 1990) and the acquisition of desiccation tolerance, while no apparent morphological changes occur. Abscisic acid and osmotic stress play an important role during embryoid maturation. Both parameters are involved in the expression of a specific set of genes and they both can inhibit precocious germination (Kermode, 1990; Skriver and Mundy, 1990; Huet and Jullien, 1992). From our experiments it is apparent that exogenous ABA promotes desiccation tolerance. However, without the addition of ABA a small percentage of the embryoids still survived the drying treatment. This might indicate that induction of desiccation tolerance resides in the developmental program of the embryoid and that it is not only due to exogenous ABA. Tolerance is lost when embryoids are switched precociously from the embryogenic program (maturation) to the germination program, which will occur when ABA is left out from the medium. During a small time window just before embryoids may commence precocious germination, they are desiccation tolerant (FIGS. 7 and 8), probably because they contain some endogenous ABA (Iida et al., 1992). Also in a double mutant of *Arabidobsis thaliana*, lacking both ABA synthesis and ABA sensitivity, some desiccation tolerance (15%) was observed during embryo development at 16 days after pollination (Koornneef et al., 1989). We only obtained 20% regrowth after dehydration with genotype "RS 1". This percentage probably is so low, because of asynchronous embryoid development: some were still too young (heart shaped), others already proceeded into the germination phase. In accordance with the experiments by Huet and Jullien (1992), inhibition of precocious germination by osmotic stress (60 g/l sucrose in the maturation medium) increased the percentage of desiccation tolerant "Trophy" embryoids to 45% in the absence of ABA (FIG. 8). In Table III we also show that high sucrose concentrations (80–120 g/l, osmotic pressure −0.6 to −1.1 MPa) with low ABA concentration (3.8 μM) gave similar results as high ABA concentration (37.9 μM) without osmotic treatment, demonstrating that osmotic stress can replace ABA. Anandarajah and McKersie (1990 and 1991) were also able to induce desiccation tolerance in somatic embryoids of alfalfa through elevated sucrose concentrations. Also the vigour of the dry alfalfa embryoids was enhanced, an effect that we have not noticed with our carrot embryoids. These data might be explained by an osmotically induced increase of the endogenous ABA concentration (Skriver and Mundy, 1990). However, it has to be realized that sucrose not only acts as an osmoticum but also as the sole carbohydrate source. Sucrose had a significant effect on the dry matter content of the embryoids (FIGS. 4 and 5). An optimal maturation protocol apparently requires both ABA and a sucrose treatment. This is further supported by the observation that embryoids after one week on ABA medium with 2% sucrose produced secondary embryoids on their axes, thereby losing their desiccation tolerance. Embryoids grown in ABA at high sucrose concentrations never showed secondary embryogenesis.

Dehydration

The rate of drying has been identified as a crucial factor during the acquisition of desiccation tolerance, not only in embryoids (McKersie et al., 1989; Seneratna et al., 1989a and b) but also in desiccation resistant nematodes (Madin and Crowe, 1975), slow drying appeared to be essential for survival. Carrot embryoids behaved similarly, only the slowly dried embryoids were able to germinate (FIG. 1). These observations implicate that during the slow drying changes occur within the organisms which protect them from the deleterious effects of dehydration. Resistant nematode species produce large amounts of the disaccharide trehalose, that protects membranes and proteins in the dry state (Crowe et al.,1987). Also in plants large quantities of di- and oligo- saccharides are found in desiccation tolerant seeds (Koster and Leopold, 1988) and pollen (Hoekstra and Van Roekel, 1988). Not only the carbohydrate content might change during dehydration but also the protein content. Nordin et al. (1991) and Grossi et al. (1992) have recently demonstrated that during drought stress a specific set of genes is expressed. Most of these genes are also induced by ABA, but some are exclusively expressed during drought stress. The resulting proteins might be crucial to survive desiccation stress. This suggestion might also explain why Iida et al. (1992) found such low germination percentages with their rapidly dried (3h) carrot embryoids. During this short drying period probably insufficient amounts of proteins and oligo-saccharides were synthesized for optimal regrowth.

Germination

The best way to measure desiccation tolerance is to determine germination. Non-germinating embryoids are not necessarily desiccation intolerant, because germination can be hindered by dormancy or by the wrong germination procedure. Embryoids are naked, viz. not protected by a seed coat and endosperm, and therefore might be very sensitive to imbibitional damage and nutritional shortage. We have demonstrated that prehydration significantly enhances regrowth (FIG. 2). The positive effect of prehydration on the germination percentage is an indication that stability of membranes may play a role in the desiccation tolerance of embryoids. Membrane phospholipids of dry organisms are in the gel phase (Hoekstra et al., 1989), which may also hold for dry embryoids. During imbibition the membrane changes from the gel phase to the liquid-crystalline phase. Such transition can cause leakage of cell solutes when free water is available for solute transport, which may be catastrophic for the embryoid. Prehydration with moist air prevents leakage, because the transition then occurs in the absence of free water. The lower germination percentage on water compared to B5 medium (Table II), might be explained by a lack of nutrition. However, the leakage measurements suggest that membrane integrity might play a role here as well. Tolerant embryoids imbibed in water leak at the same rate as intolerant embryoids in B5 medium.

Tolerance induction using LAB 173-711 (an ABA analog)

The same set of experiments has been carried out with LAB 173-711 instead of ABA. The results are depicted in Table III.

TABLE III

Effect of LAB concentration on the desiccation tolerance of different organs of carrot embryoids. Embryoids were slowly dehydrated at controlled RH and prehydrated in moist air for four hours before imbibition in B5 medium.

| regrowth | LAB ($\mu$M) | | | | | |
|---|---|---|---|---|---|---|
|  | 0 | 2 | 5 | 20 | 40 | 60 |
| roots | − | + | + | ++ | ++ | ++ |
| shoots | − | − | ± | + | ++ | ++ |

−= none;
±= poor;
+= fair;
++= good

These regrowth data are similar to those of embryoids treated with ABA. It can be concluded that LAB 173-711 is able to induce desiccation tolerance at the same concentration as ABA, although it is suggested to be four times more effective than ABA.

Comparison of Zygotic and Somatic Embryogenesis

In FIG. 6 we have shown the development of seeds and embryoids of Daucus carota on the basis of the moisture content. The curves look similar but the main difference between the two types lies in the time that the embryo(id)s need to decrease the moisture content from 3 to 0.5 g $H_2O$/g DW, which coincides with the maturation part of the development. The zygotic embryo has a prolonged maturation phase with an extended reserve accumulation as compared to the embryoid. We have to take into account that the data are from whole seeds, that is from embryos with endosperm. The condensed maturation of the embryoids might have reduced the regrowth potential, because the embryoids may not have been able to synthesize all the necessary proteins, lipids and carbohydrates in the 10–12 days maturation period. In contrast zygotic embryos have a 40–50 days maturation phase. In this respect somatic embryogenesis does not mimic zygotic embryogenesis.

In conclusion our data clearly demonstrate that it is possible to induce complete desiccation tolerance in embryoids of different genotypes of carrot.

Tolerance Induction in Cucumber

We have got two lots of globular cucumber embryoids from Ahrensburg, which we have used to perform two ABA experiments. ABA (2–20 $\mu$M) added to liquid or semi-solid B5 media with developing globular cucumber embryoids is also capable, like with carrot embryoids, to inhibit the precocious germination. At too low ABA concentrations (0.01 1.0 $\mu$M) embryoids demonstrated radicle protrusion and greening of the "cotyledons". whereas the embryoids on high ABA media continued their embryoids development to more or less torpedoshaped stages. The embryoid development on solid medium was clearly better than on liquid medium. In suspension only very little cotyledons were formed, whereas embryoids on agar developed nice cotyledons. We also were able to dehydrate some of these cucumber embryoids and callus and the regrowth data are shown in Table II. Plant material was slowly dried and prehydrated in moist air before imbibition in B5 medium.

TABLE II

Effect ABA and sucrose on the development of desiccation tolerance in cucumher embryoids and callus.

| Sucrose (gr./1) | ABA ($\mu$M) | | | |
|---|---|---|---|---|
|  | 0 | 5 | 10 | 15 |
| 20 | − | − | − | − |
| 60 | − | C/R | C/R | C/R |

C: callus growth;
R: root elongation

These data clearly demonstrate that also cucumber can acquire desiccation tolerance and also ABA relatively high concentrations of are necessary to survive dehydration to low moisture contents.

Coating Experiments

In order to avoid problems with rehydration of the embryoids and thus with germination thereof coatings allowing for imbibation of the embryoids were developed.

Plant material: The same plant materials were used as described in material and methods.

In this first experiment the basic coating consisted of parafinne 4444 (Paramelt Syntac), with an additive coating consiting of sucrose.

Coating mix: A: 0% sucrose
B: 0.5% sucrose
C: 1% sucrose
D: 5% sucrose
E: 10% sucrose
H: 50% sucrose Embryoids are imbibed in the melted coating mix (melting temperature 65° C.). They are harvested and cooled in ethanol or waters (under stirring). The embryoids are (after a rest period) allowed to germinate at 25° C. in the light.

Results

| number | plant material | coating | cool sol. | behav. | germination | remarks |
|---|---|---|---|---|---|---|
| 01 | Z4.8137 | − | — |  | 100% | control |
| 02 | Z4.2973 | − |  |  | 75% | control |
| 03 | Z4.8137 | A | water | float | 0 |  |
| 04 | Z4.2973 | A | water | float | 0 |  |
| 05 | Z4.8137 | B | water | float | 0 |  |
| 06 | Z4.2973 | B | water | float | 0 |  |
| 07 | Z4.8137 | C | water | float | 0 |  |
| 08 | Z4.2973 | C | water | float | 0 |  |
| 09 | Z4.8137 | D | water | float | 0 |  |
| 10 | Z4.2973 | D | water | float | 0 |  |
| 11 | Z4.8137 | E | water | float | 0 |  |
| 12 | Z4.2973 | E | water | float | 0 |  |
| 13 | Z4.8137 | H | water | sink | 0 |  |
| 14 | Z4.2973 | H | water | sink | 0 |  |

- Cooling with alcohol did not work well because the drops formed "mushrooms" instead of "round pills". The cooling solution is probably to apolar. Therefore only water was used as a cooling agent.
- usage of a magnetic stirrer improves the shape of the pills, only when the droplets are sinking in the water. The shape might be improved if we can make the cooling solution more polar through the addition of salts.

sucrose crystals did not distribute well through the coating mix, especially the large crystals. Therefore it was difficult to get a homogenous coating.

Possible reasons for the lack of germination after the encapsulation might be;
  1: water supply is blocked through the wax, there are to less windows for sufficient water supply
  2: lack of oxygen supply
  3: heat shock of the treatment might damage the seeds
  4: toxicity of the wax Conclusion The used coatings were impermeable for water, therefore no germination occurs. In order to improve the permeability for water of the coatings we have to add more filling materials.

Breaking the Water Impermeability of the Wax Layer Through the Addition of Filling Materials The same plant materials as in the previous experiment were used the same basic coating was used. The additive coating was sucrose (grinded with mortar mill) and/or Wimer 130® (Ankerpoort).

Coating Mix:

| coat-number | paraffine (gr) | wimer 130 (gr) | sucrose (gr) |
|---|---|---|---|
| A002 | 2 | 1 | 0 |
| B002 | 2 | 2 | 0 |
| C002 | 2 | 3 | 0 |
| D002 | 2 | 4 | 0 |
| E002 | 2 | 1 | 1 |
| F002 | 2 | 2 | 1 |
| G002 | 2 | 3 | 1 |
| H002 | 2 | 4 | 1 |

Cooling: water (no magnetic stirrer)
Melting temperature: 65° C. and 95° C.
Results

| coat-number | shape | behaviour | remarks |
|---|---|---|---|
| A002 | half globule | float | |
| B002 | half globule | float | |
| C002 | globular | sink | |
| D002 | nice globule | sink | |
| E002 | half globule | float | |
| F002 | nice globule | sink | |
| G002 | nice globule | sink | |
| H002 | rough globule | sink | very viscous |

All structures were smooth on the outside when they were cooled in water. The outside layer only contained wax and therefore the pills were still water impermeable. When the droplets were cooled in ethanol the outside also contained some filling materials but after imbibition in water these crystals were released from the pill and a smooth waxy layer remained, with was again water impermeable. In order to lower the viscosity of the HOO2 coating we have increased the melting temp to 95° C., but this had not much effect, probably because of the high amount of filling materials.
Possible solution; addition of a solvent (e.g. methanol)

Conclusion

The used coatings were still impermeable for water, because there was still to much wax at the outside of the pill. This was the reason to skip the seed encapsulation and germination test. In order to improve the permeability for water of the coatings we have to lower the amount of wax by addition of other more polar materials.

Acquisition of water permeability of the coating layer through the addition of PEG.

The same plant materials as in the previous experiments were used.

The basic coatings were paraffine 4444 and/or PEG 3400.

The additive coating comprised sucrose (grinded with mortar mill) and/or Wimer 130®.

Coating mix:

| coat-number | paraffine (gr) | PEG 3400 (gr) | wimer 130 (gr) | sucrose (gr) |
|---|---|---|---|---|
| A03 (D002) | 2 | 0 | 4 | 0 |
| B03 | 1.5 | 0.5 | 4 | 0 |
| C03 | 1 | 1 | 4 | 0 |
| D03 | 0.5 | 1.5 | 4 | 0 |
| E03 | 0 | 2 | 4 | 0 |
| F03 (H002) | 2 | 0 | 4 | 1 |
| G03 | 1.5 | 0.5 | 4 | 1 |
| H03 | 1 | 1 | 4 | 1 |
| I03 | 0.5 | 1.5 | 4 | 1 |
| J03 | 0 | 2 | 4 | 1 |
| K03 | 0.5 | 1.5 | 0 | 0 |
| L03 | 0 | 2 | 0 | 0 |

Melting temperature: 65° C./81° C.
Results

| coat-number | shape | behaviour | remarks |
|---|---|---|---|
| A03 | droplets | | liquid |
| B03 | — | | to viscous |
| C03 | — | | to viscous |
| D03 | — | | to viscous |
| E03 | — | | viscous |
| K03 | droplets | float | liquid |
| L03 | droplets | sink | viscous |

Mixing PEG with wax was not successful when there is also Wimer 130 is added, because the mix was not homogenous and top viscous to form droplets. Without the filling material the mix of wax and PEG (K03) was homogenous and viscous, but still was able to form droplets. But during the cooling in water the materials separated, thereby the wax formed a impermeable layer on the outside of the drops. Sometimes the PEG on the inside was wet and thus had gained water, which is undesirable. When cooled in the air the Wax formed a layer on top of the PEG, because PEG is heavier than wax. Droplets of E03 and L03 contained of only polar materials and therefore dissolved easily in water. This might give problems with the rehydration of the embryoids. Water transport is probably too easy in these coatings. To retard this water transport addition of low amounts of wax or the addition of amphyphilic compounds like fatty acids might work. Cooling in water is undesirable because the pill has to be somewhat permeable for water. When cooled in water the imbibition will start immediately. Water also promotes the apolar compounds of the mix to settle on the outside thereby blocking the water transport. The use of a apolar cooling liquid might be much better.

No encapsulation and germination test were performed because the mixes did not fulfill our needs.

Conclusion

PEG can be used as a basic coating material, but we have to control the water transport through the addition of wax or other apolar materials. Wax may not be desirable as basic coating material because it is to apolar and thereby restricts the water transport too much. The used coatings were still impermeable for water, because there was still too much wax at the outside of the pill. This was the reason to skip the seed encapsulation and germination test. In order to improve the permeability for water of the coatings we have to lower the amount of wax by addition of other more polar materials.

Restriction of water transport in coating based on PEG 3400 through addition of F 312 wax coating (Keyser and Mackay)
Basic coating: PEG 3400 (Harb/Heybroek).
Additive coating: F 312 wax coating (this was used instead of paraffine 4444 because of its color.
Coating mix: 0.2%; 1%; 2%; 4%; 10%; 20% and 30% (K03) addition of F 312 wax coating to the basic coating.
Cooling: air, water and sunflower oil
Melting temperature: 81° C.
Results In all concentrations, except 30%, the wax formed droplets inside the PEG matrix. We hoped to get thinner wax layers on the outsine of the PEG. Only at 30% such a layer is formed but it is too thick. The water transport was not restricted by these droplets, because all the pellets dissolved very easily in water. Water could not be used as the cooling liquid. The oil worked well (only 20% mix was tested) but the congealing was rather slow and therefore the whole pellet (in- and outside) was soaked with oil. This might be profitable for the water transport, but it might give practical problems. The pellets cooled in oil dissolved in water.

Conclusion

A mix of PEG with wax is not the solution for an optimal water transport. It might be better to use materials that are less apolar than wax, like fatty acids. Changing the polarity of the cooling liquid might also help in this case.

Formation of water permeable windows in apolar basic coating through the addition of relatively light materials.
Basic coating: paraffine 4444 (0.9 gr/cm$^2$) 4 gr
Additive coating:

Aerosil 200 (0.05 gr/cm$^2$) 0.1 gr: A05

Dicalite 418 (0.21 gr/cm$^2$) 0.4 gr: B05

Pumice 0–90μ (MCA) (0.90 gr/cm$^2$) 2.7 gr: C05

Pumice 40–250μ (MCA) (0.90 gr/cm$^2$) 2.7 gr: D05
cooling: water+tween, alcohol+tween
melting temperature: 65° C.
Results Pumice 0–90μ seems to be the best material for filling. We have tested this by monitoring with the binocular the formation of air bubbles at the surface of the pills. Because water goes into the pill while the air is pushed out. This does not mean that this is also the best for pills with seeds. This is going to be tested in the next experiment. Pumice 40–250μ behaved as a filling material with high density, that means that it sinks to the bottom. No windows are formed in the outside layer of the pill. The other two materials had no effect during the air bubble test, this might be due to the low amounts that were added to the basic coating. Alcohol can also be used as cooling fluid, and has the advantage that the outside of the pills are sterile. This might be necessary for the germination of embryoids.

Acquisition of water permeability of the coating layer through the addition of lighter filling materials
Basic Coating: parffine 4444
Additive Coating: sucrose (grinded with mortar mill), Wimer 130 (Ankerpoort), Pumice 0–90μ
Coating mix:

| coat-number | paraffine (gr) | pumice (gr) | wimer 130 (gr) | sucrose (gr) |
|---|---|---|---|---|
| A06* | 2 | 2 | 1 | 0 |
| B06* | 2 | 1.5 | 2 | 0 |
| C06 | 2 | 0.5 | 3 | 0 |
| D06* | 2 | 0.5 | 4 | 0 |
| E06* | 2 | 1.2 | 1 | 1 |
| F06 | 2 | 0.4 | 2 | 1 |
| G06* | 2 | 0.2 | 3 | 1 |
| H06* (H002) | 2 | 0 | 4 | 1 |

*: indicates that the mix was diluted with acetone to improve the fluidity

Cooling: alcohol+Tween 20 (5.04.012) 2 droplets per 1000 ml
Melting temperature: 65° C.
Results Dilution of the coating mix with acetone works very well during the preparation of the pills. The mix forms better droplets because it is less viscous. The effect of the acetone on the seeds has still to be seen. The germination figures did not demonstrate any negative effect of acetone. It even might be considered that addition of acetone has a positive effect on the germination of lettuce seeds, because it makes the coating layer more open, which might promote water transport or makes the coating easier to break through which the seeds can more easily grow out.
Germination test:
temp 25° C., light

| coat-number | Z4.2973 | Z4.8137 | remarks |
|---|---|---|---|
| control | 90% | 100% | |
| A06* | 8% | 92%[1] | perfect imbibition |
| B06* | 16% | 92%[1] | perfect imbibition |
| C06 | 33% | 80%[2] | perfect imbibition |
| D06* | 36% | 100% | perfect imbibition |
| E06* | 0% | 0% | poor imbibition |
| F06 | 0% | 0% | poor imbibition |
| G06* | 0% | 0% | poor imbibition |
| H06* (H002) | 0% | 0% | poor imbibition |

[1]: the pills that were scored as no germination contained seeds which were germinated, but had not yet grown out of the coating.
[2]: the pills that were scored as no germination contained seeds which were indeed not germinated. These pills might be somewhat harder, because no acetone was used.

The poor imbibition of the seeds of the last four treatments was clearly visible, because the embryos were still glassy, whereas well imbibed embryos are white and tough. On the other hand the coating material of these pills seemed to contain more water than the first four treatments. This might be due to the sucrose which will attract water, but this attraction inhibits the seed imbibition. We might have to look for other non osmotic materials to serve as nutrition for the embryoids like starch or proteins, or lower concentrations of sucrose. FIG. 9. shows the course of water uptake of A06 and D06 pills without seeds. This measurement was done in order to get an idea about the availability of water and water transport during the imbibition on filter paper. In the future this might be an easier method than a germination test to check if the coating material satisfies our requirements.

Conclusion

We are able to create water permeability through the addition of lighter filling materials, but we still have to test if the water transport is also sufficient for the carrot embryoids. Measurement of the flux of water uptake might be very useful in this case.

The lower germination of the carrot seeds might be due to the tough coating, whereas lettuce seeds are able to grow out of the pill.

Addition of sucrose to the coating completely inhibits the germination of both types of seeds. The osmotic activity of sucrose causes the poor imbibition.

Reduction of water permeability of a coating mix based upon a water soluble wax through the addition of apolar fatty acids. Monitoring the effect of water soluble wax and cooling liquid on the germination of carrot and lettuce seeds.

Basic coating: PEG 3400
Additive coating: Pumice 0–90μ,
  Wimer 130,
  stearic acid (Merck),
  palmitic acid (Merck)
cooling: sunflower oil+tween,
  water+tween,
  ethanol+tween,
  methanol+tween
melting temperature: 65, 75, 85° C.
coating mix:

| number | PEG 3400 | wimer 130 | pumice | palmitic acid | stearic acid |
|---|---|---|---|---|---|
| E07 | 3 gr. | 3 gr. | 1 gr. | — | 1 gr. |
| F07 | 3 gr. | 3 gr. | 1 gr. | 1 gr. | — |

Results

E07 had to be melted at 75° C. because stearic acid only dissolved in the mix at this higher temperature. To encapsulate the seeds the mix had to be heated to 85° C. because at lower temperatures the mix congealed to fast. It was very difficult to make nice droplets, also at the higher temperature. This might give practical problems in the future. Insoluble wax works much easier. F07 could only be encapsulated at 75° C., whereas palmitic acid dissolved already at 65° C. in the mix.

Both mixes could be cooled with all four cooling liquids, but the four cooling liquids all resulted in other kinds of pills. Especially the surface and the shape were altered. The air bubble test showed that water was taken up by the pills independent of the cooling liquid. It seemed that the pills made in ethanol gave more air bubbles, but this must be confirmed with a water uptake test. We only tested F07 pills made in water (see FIG. 10) to get experience with the test and to see if the test is accurate enough. The test worked out very well, but in the case of a basic coating of PEG 3400 water uptake can not be measured through weight increase. The pill looses weight because the basic coating dissolves in the imbibition medium. In this case only the germination test can tell if the pill satisfies our requirements.

Germination test:
temp 25° C., light

| coating | plant material | cooling | germination 4 days | 7 days |
|---|---|---|---|---|
| controle | Z4.8137 | — | 100 | 100 |
|  | Z4.2973 | — | 0 | 75 |
| E07 | Z4.8137 | alc. | 100 | 100 |
|  |  | oil | 0 | 72 |
|  | Z4.2973 | alc. | 0 | 64 |
|  |  | oil | 0 | 8 |
| F07 | Z4.8137 | alc. | 100 | 100 |
|  |  | oil | 0 | 88 |
|  | Z4.2973 | alc. | 0 | 75 |
|  |  | oil | 0 | 45 |

Additional results: the pills did not disintegrate during the imbibition through the dissolvation of the basic coating in the water. When the seeds germinated the pills broke in two pieces.

Conclusions

From the germination data presented in the table we can draw the following conclusions:
  water soluble wax can be used as a basic coating. It does not inhibit the germination, but there are some practical problems like the formation of nice droplets
  the cooling liquid has a clear effect on the germination energy of the seed lots possibly caused through the regulation of water uptake. Cooling with oil gives the pill a more apolar character because some oil is absorbed by the coating mix. Therefore the coating might enhance the inhibition of the water uptake. But eventually the seeds become completely imbibed and are able to germinate. It has to be tested which cooling liquid gives the best regulation of water uptake for the carrot embryoids. Cooling with alcohol might result in a too rapid water uptake.
  the effect of the fatty acids in the mix is small, but it seems that stearic acid gives better results.

Testing pumice 0–30μ (Profiltra) (a fine (0–25 μm) and light (0.9 gr/cm3) filling material) for its water permeability in a wax coating. (comparison exp. 06)

Basic coating: paraffine 4444
Additive coating: Pumice 0–30μ,
  Wimer 130,
  acetone
coating mix:

| coating number | paraffine | pumice | wimer 130 |
|---|---|---|---|
| A08 | 7.5 | 5 | 0 |
| B08 | 6 | 4 | 2 |
| C08 | 5 | 3 | 4 |
| D08 | 4 | 2 | 6 |
| E08 | 4 | 1 | 8 |

To improve the fluidity of all the mixes aceton was added.
Cooling: ethanol+tween
Melting temperature: 65° C.
Results Through the addition of more then 3 gr. Pumice 0–30μ to the mix, it became too solid. It was not possible to make the mix fluid with acetone, therefore we had to raise the amount of paraffine and still add acetone. Only A08 and E08 were used for water uptake profiles. These profiles are made with 40 pills (+1.1 gr.). The water absorption profiles are shown in FIG. 22. There is not much difference between the two coating mixes. The pills still absorb water after 11 days.

Germination Test
temperature: 25° C., light

| coating | Z4.8137 | | Z4 2973 | |
| --- | --- | --- | --- | --- |
| number | 4 days | 7 days | 4 days | 7 days |
| control | 100% | 100% | 58% | 84% |
| A08 | 50% | 100% | 0% | 50% |
| B08 | 25% | 100% | 0% | 25% |
| C08 | 8% | 100% | 0% | 8% |
| D08 | 16% | 100% | 0% | 25% |
| E08 (D06) | 33% | 100% | 0% | 16% |

All coating mixes give with both seed lots a retardation of the germination. But in the case of Z4.8137 no effect was demonstrated on the final germination percentage after 7 days, whereas for Z4.2973 it seems that the addition of Wimer 130 decreased the final germination percentage.

This is in contrast with the previous experiment, because there it seemed that addition of wimer 130 increased the germination. The difference between A08 and E08 (amount of Wimer 130) in the case of Z4.2973, can not be explained by water transport, because E08 absorbed even more water then A08 (see FIG. 11).

The final germination of coated Z4.2973 seeds never reached the germination level of the control, despite the good rehydration of the seeds. It might be that oxygen supply is not sufficient, or the pills might be to tough.

Conclusion

Measuring water absorption profiles can be very useful for the understanding of the behaviour of coated seeds. Pumice 0–30$\mu$ can be used for filling material of waxy coatings Testing other wax types in respect to paraffine 4444.
Plant material: Z4.8137, Z4.2973
Basic coating: Ozokerite® D306 (Keyser & Mackay) (57–59° C.),
Ciragref 80 slabs (Keyser & Mackay) (58–63° C.),
paraffine 2050/vk60 (Paramelt Syntac) (58–60° C.)
Additive coating: Wimer 130®,
Pumice 0–90$\mu$

| coating mix | ozokerite | ciragref | paraffine | wimer 130 | pumice |
| --- | --- | --- | --- | --- | --- |
| A09 | 4 | | | 6 | 0.5 |
| B09 | | 4 | | 6 | 0.5 |
| C09 | | | 4 | 6 | 0.5 |

Cooling: water+tween,
methanol+tween,
ethanol+tween,
sunflower oil+tween
melting temp: 75° C.
Results Ciragref did not fulfill our requirements, it was too viscous at 75° C. The other two waxes were perfect. They made very nice droplets in all cooling liquids. With the bubble test the pills cooled in ethanol gave the best results.

Production of a dry embryoid pill with coating A08.
Testing if carrot embryoid survive coating protocol.

Plant material: Dry carrot embryoids (cv "Trophy") produced in April 1993 (experiment BT9, Wageningen). Dry embryoids were stored at 5° C. and 30% RH for more than 1,5 year.
Basic coating: paraffine 4444
Additive coating: Pumice 0–30$\mu$ (mix A08, see before) acetone
Melting temperature: 75° C.
Cooling liquid: ethanol+Tween Storage: after the ethanol cooling the embryoid pills were collected in a sterile plastic petri-dish to dry. When they were dry (at least two hours) they were brought to a laminar air flow cabinet to be imbibed and germinated under sterile (aseptic) conditions.

Germination: in a 6 mm petri dish with 3 autoclaved filter papers (Whatman nr 3) and 4.5 ml hormone free B5 medium with 20 gr./l sucrose (Gamborg et al, 1968). Temperature 25° C., in the light (cell 2 seed tech).

Germination was performed without a 4 hours prehydration treatment at high relative humidity, which is necessary for imbibing naked embryoids because of occurrence of imbibitional damage.

Results

Coating of embryoids was easier than seeds because they are much smaller. There were no problems with the sterility of the whole procedure, because no fungi or bacterial growth was found during the germination test.

After 24 hours of imbibition, the embryoids were already coming out of the coating material (photographs 1–4) (FIG. 12). This is caused by the swelling of the embryoids,. It indicates that the coating material permeates B5 medium and it is not too tough to be pushed away by the swelling embryoids. The embryoids develop enough force to get out of the coating. After 3 days of imbibition the first root elongation was visible (photographs 5–7) (FIG. 12). The embryoids were viable and had survived the coating treatment. The next day the hypocotyls of the embryoids became green and the roots continued their elongation (photographs 8–11) (FIG. 12). After one week complete plantlets were developed (photographs 12-13) (FIG. 12). The germination percentage after one week was 50% (15/30).

Conclusion

It is possible to encapsulate dry carrot embryoids with a water free coating layer without the loss of viability. With this coating layer the water transport was in such a way that the prehydration treatment became redundant.

BRIEF DESCRIPTION OF THE DRAWING

The file of this patent contains at least one drawing executed in color. Copies of this patent with color drawing(s) will be provided by the Patent and Trademark Office upon requesting payment of the necessary fees.

FIG. 12 shows photographs 1–10 giving the swelling of dried tolerance induced carrot embryoids coated as described in the last of the coating experiments.

Figure 1:
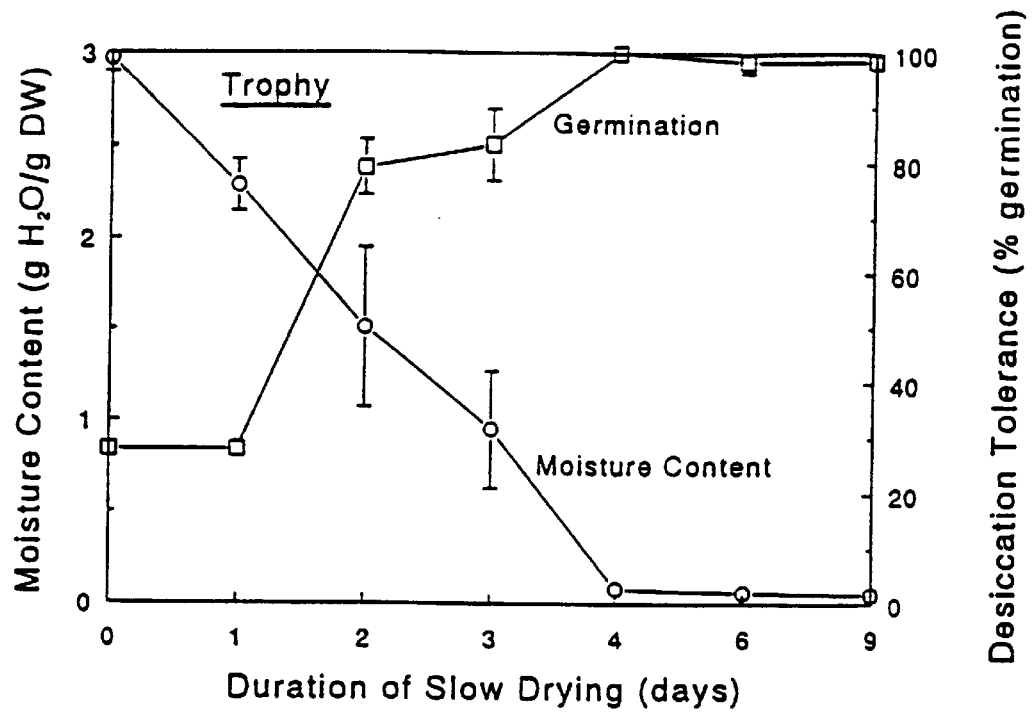
FIG. 1: Effect of slow drying on germination of dry Daucus carota embryoids (genotype "Trophy"). The embryoids were cultured for one week on OB5 medium followed by four days on maturation medium with 37.9 $\mu$M ABA and 60 g/l sucrose. At intervals during slow drying, the embryoids were rapidly dried in sterile air for four hours to 0.05 g $H_2O$/g DW. Before imbibition in OB5 medium, the embryoids were prehydrated in moist air for four hours. The moisture content data are the means±SD of four replicates, the germination data are the means±SD of duplicate measurements.
Figure 2:
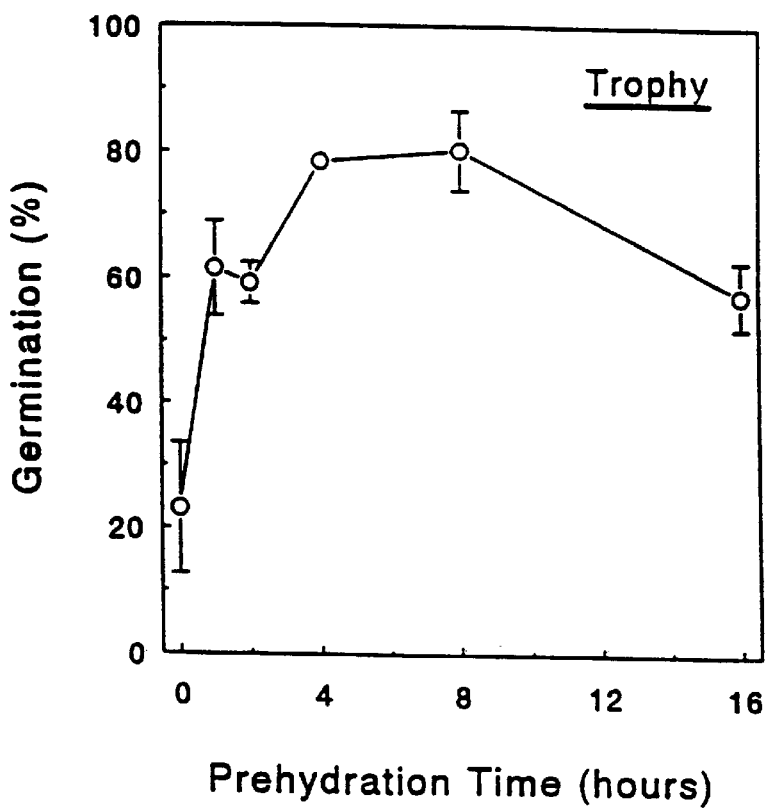
FIG. 2: Influence of duration of moist air pretreatment on the germination of Daucus carota embryoids (genotype "Trophy"). The embryoids were cultured one week on OB5 medium followed by four days on maturation medium with 37.9 μM ABA and 60 g/l sucrose. The embryoids were slowly dried for three days at 75%, 50% and 30% RH each, to a moisture content of 0.05 g $H_2O$/g DW. The germination data are the means ± SD of duplicate measurements.
Figure 3:
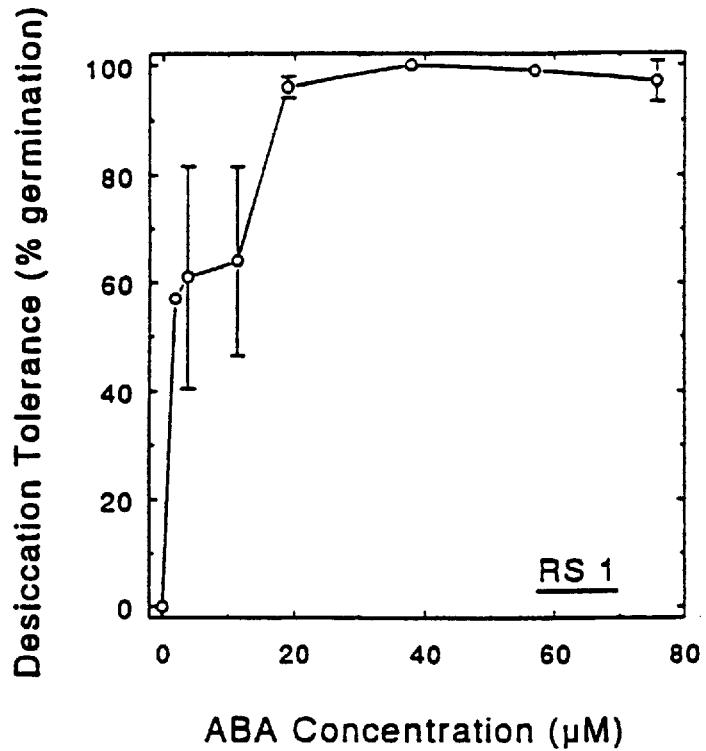
FIG. 3: Effect of ABA concentration on the desiccation tolerance of Daucus carota embryoids (genotype "RS 1") after 20 days in culture. ABA was added on the seventh day of the culture. The embryoids were successively dried for three days at 75%, 50% and 30% RH, to a moisture content of 0.05 g $H_2O$/g DW. Before imbibition in OB5 medium, the embryoids were prehydrated in moist air for four hours. The germination data are the means±SD of two or four replicates.
Figure 4:
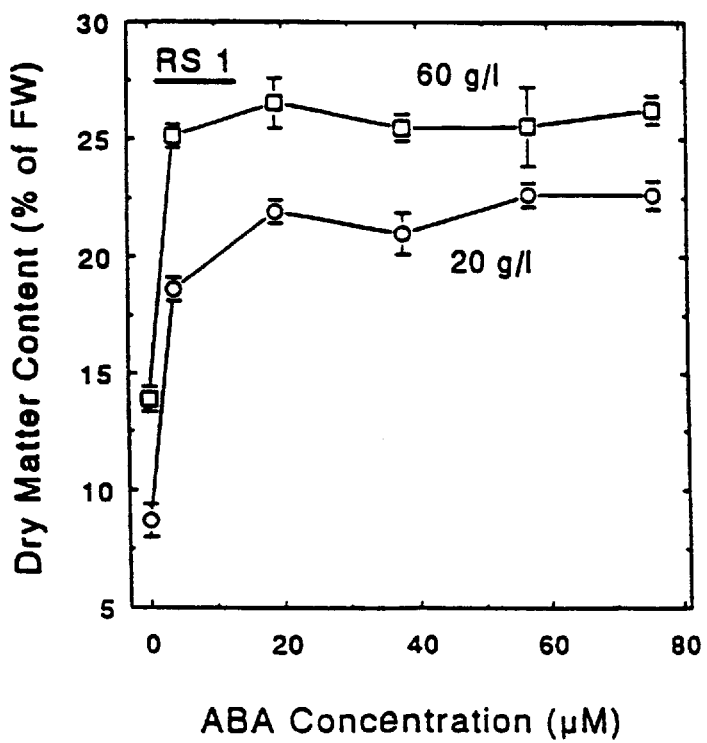
FIG. 4: Effect of ABA on dry matter content of Daucus carota embryoids (genotype "RS 1") after 20 days in culture. The embryoids were cultured on OB5 medium. On day 7 the embryoids were transferred to media containing different ABA concentration and either 20 g/l (-O-) or 60 g/l sucrose (- -). The data are the means±SD of triplicate measurements.
Figure 5:
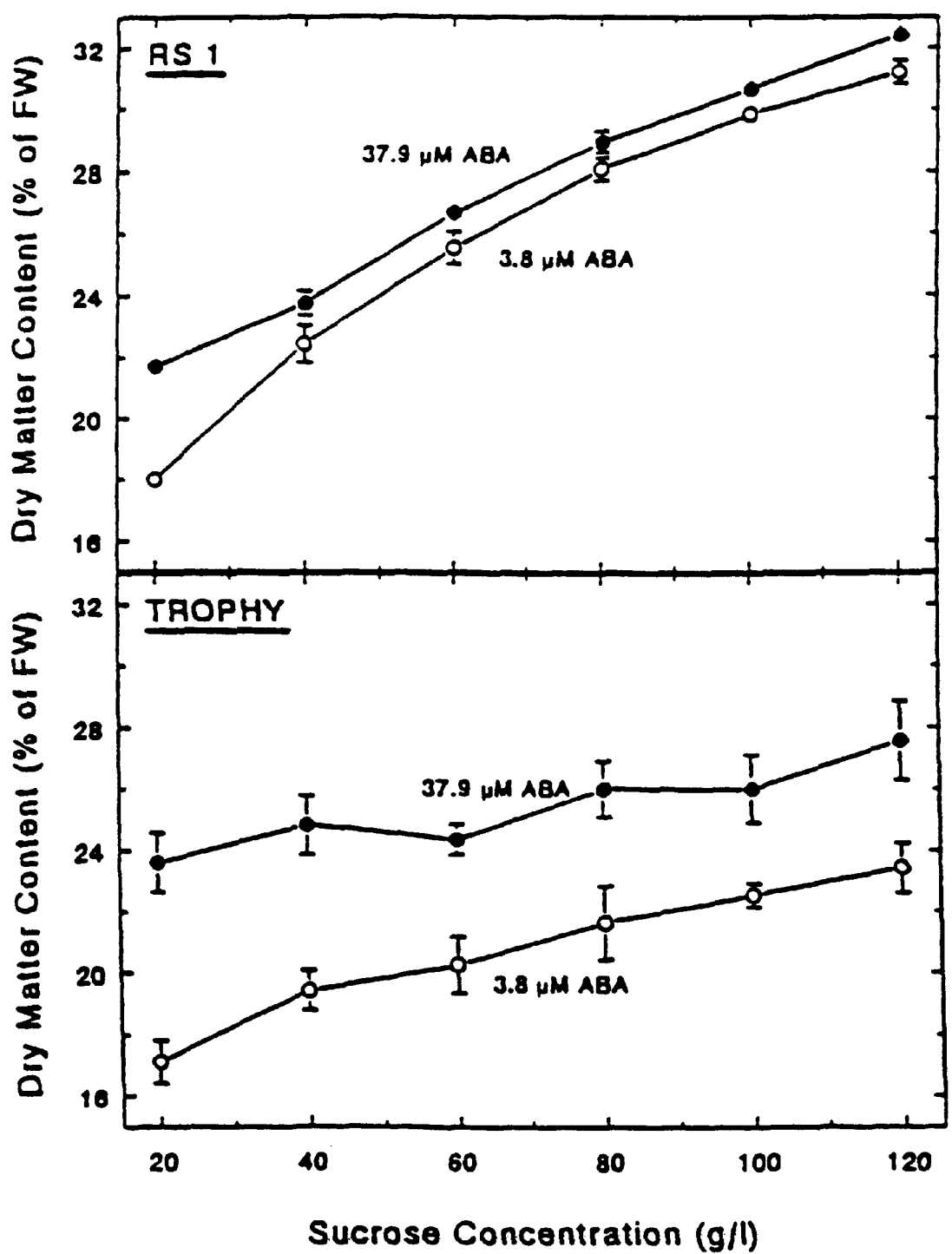
FIG. 5: Effect of sucrose concentration on dry matter content of Daucus carota embryoids after 20 days in culture. The embryoids were cultured on OB5 medium. On day 7 the embryoids were transferred to media containing different sucrose concentration and either 3.8 (-O-) or 37.9 μM ABA (- -). The data are the means±SD of triplicate measurements.
Figure 6:
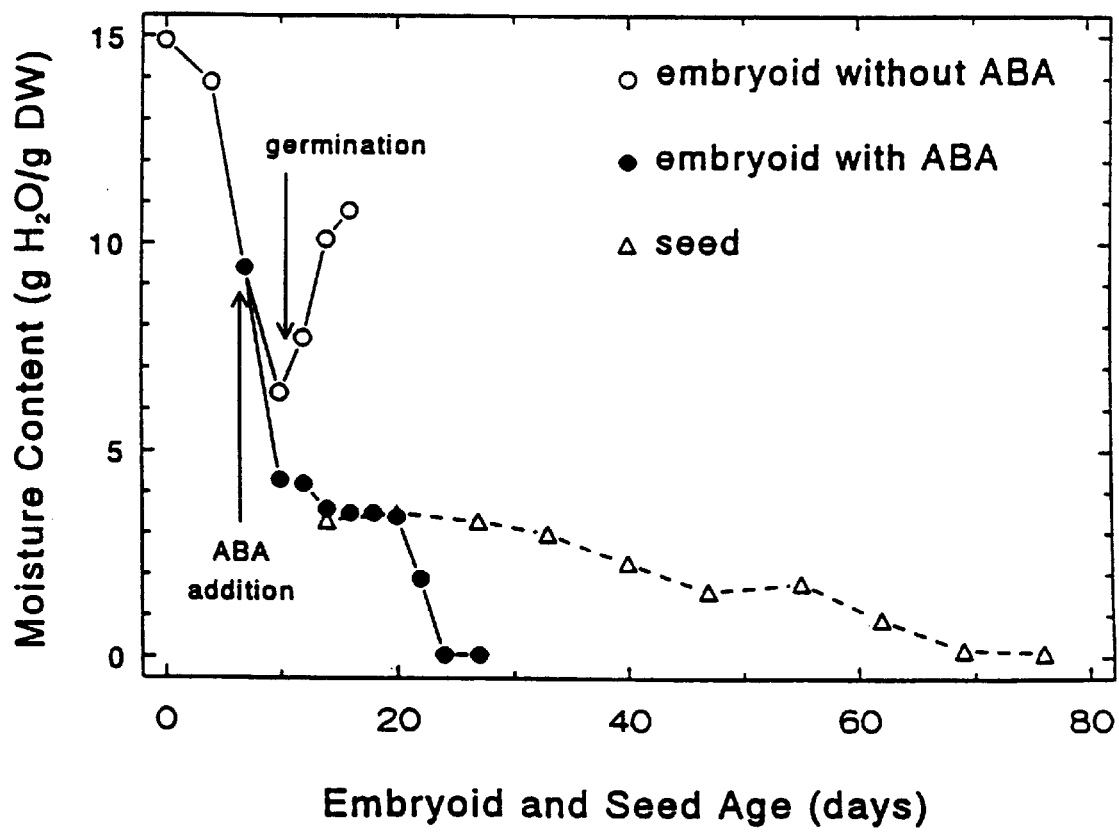
FIG. 6: Changes in moisture content during development of Daucus carota embryoids (genotype "RS 1"), with or without ABA, and of seeds of the same species. ABA (37.9 μM) was added on the seventh day of the culture. After 20 days the embryoids, treated with ABA, are slowly dried above saturated salt solutions as described in FIG. 2. The seed moisture content data are redrawn from Gray and Steckel (1982).
Figure 7:
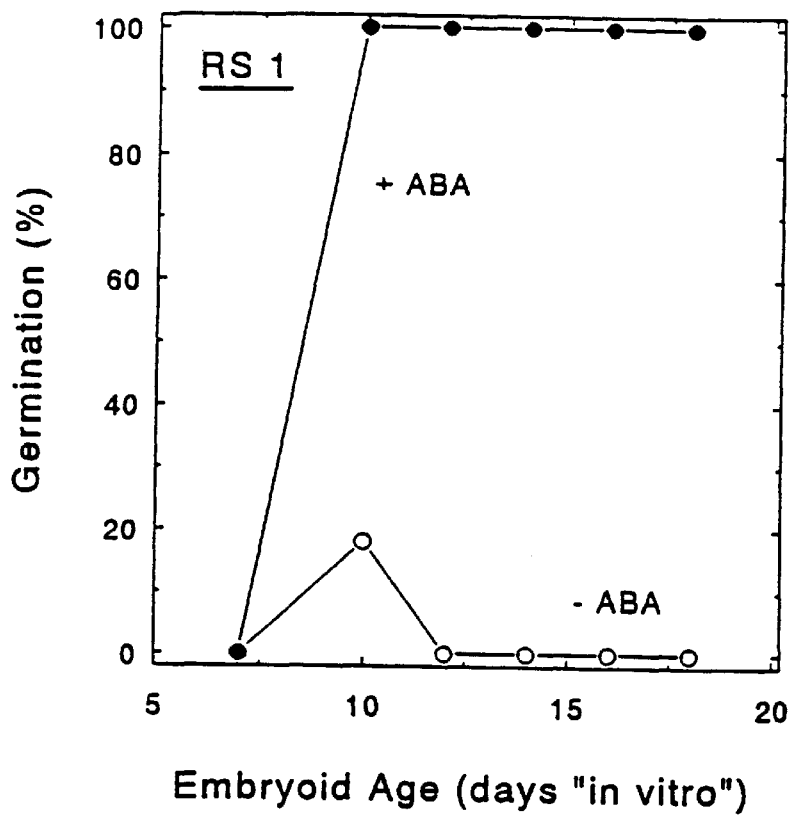
FIG. 7: Influence of ABA on the development of desiccation tolerance of Daucus carota embryoids (genotype "RS 1"). Embryoids were grown on B5 medium with 20 g/l sucrose throughout the culture period. On day 7 the embryoids were transferred to fresh B5 media either without (-O-) or with 37.9 μM ABA (- -). The embryoids were removed from the media after the indicated cultivation periods. Before germination embryoids were slowly dried. See FIG. 3 for description of slow drying and germination method.
Figure 8:
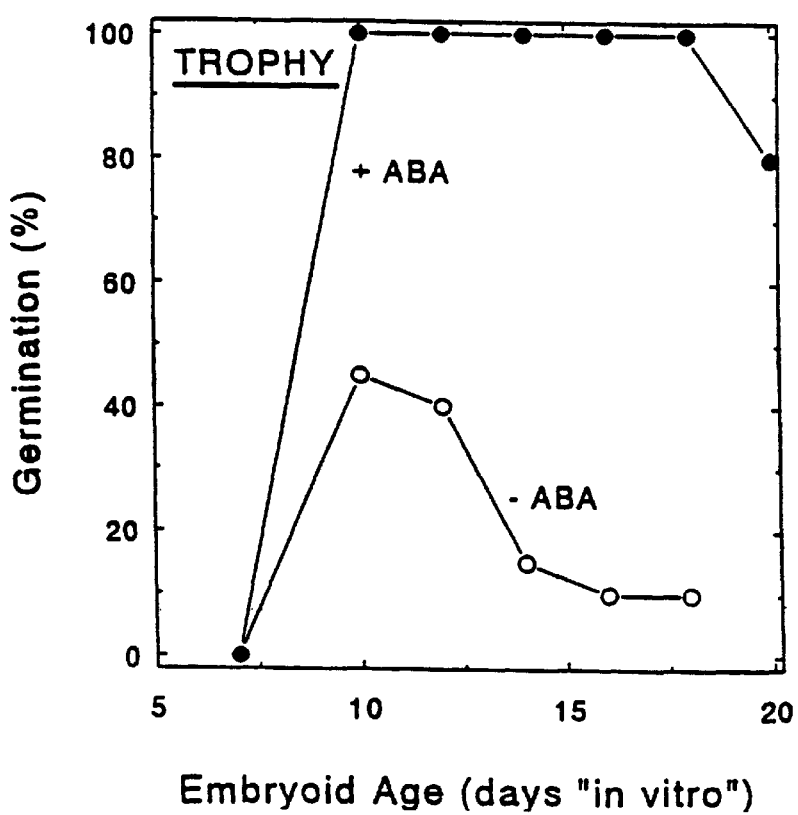
FIG. 8: Influence of ABA on the development of desiccation tolerance of Daucus carota embryoids (genotype "Trophy"). Embryoids were cultured the first week on B5 medium with 20 g/l sucrose and afterwards on B5 medium with 60 g/l sucrose. On day 7 the embryoids were transferred to fresh B5 media either without (-O-) or with 37.9 μM ABA (- -). The embryoids were removed from the media after the indicated cultivation periods. Before germination embryoids were slowly dried. See FIG. 3 for description of a slow drying and germination method.
Figure 9A:
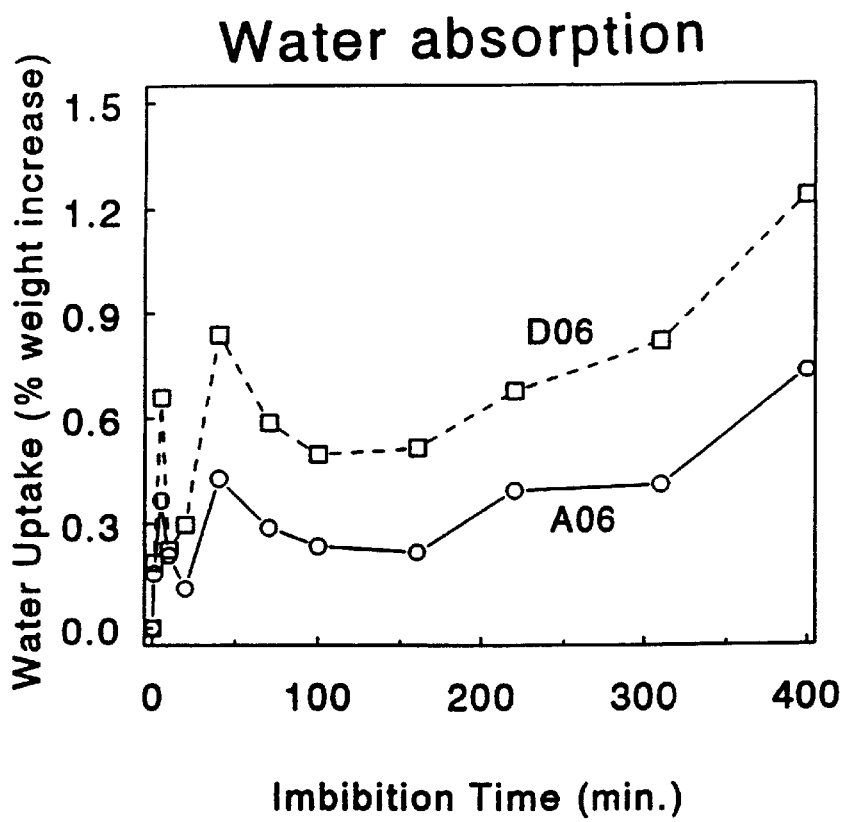
FIGS. 9A and 9B show the course of water uptake of A06 and D06 pills without seeds.
Figure 9B:
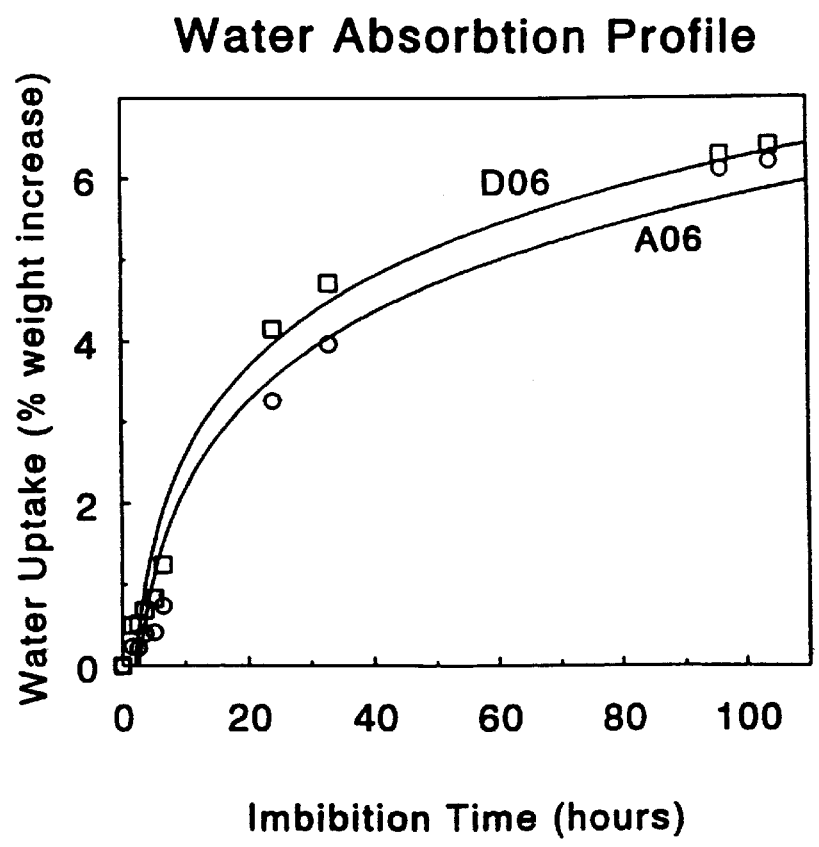
Figure 10A:
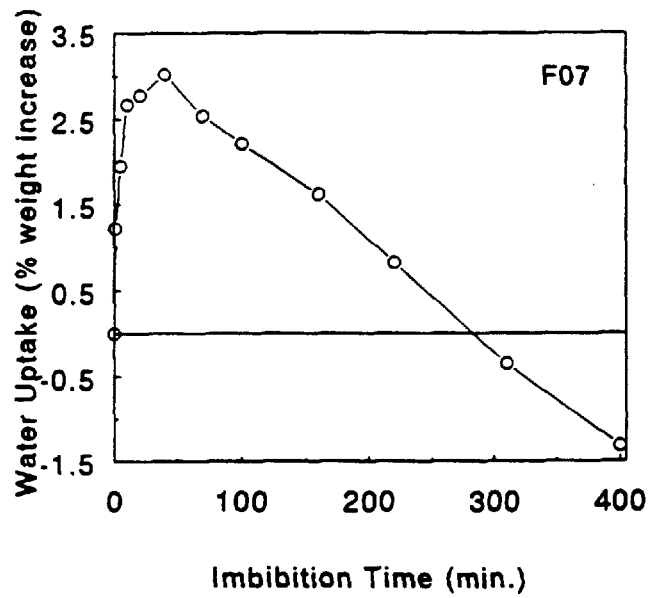
FIGS. 10A and 10B show the relationship between water uptake and imbibition time for coating F07 as described in the experiments.
Figure 10B:
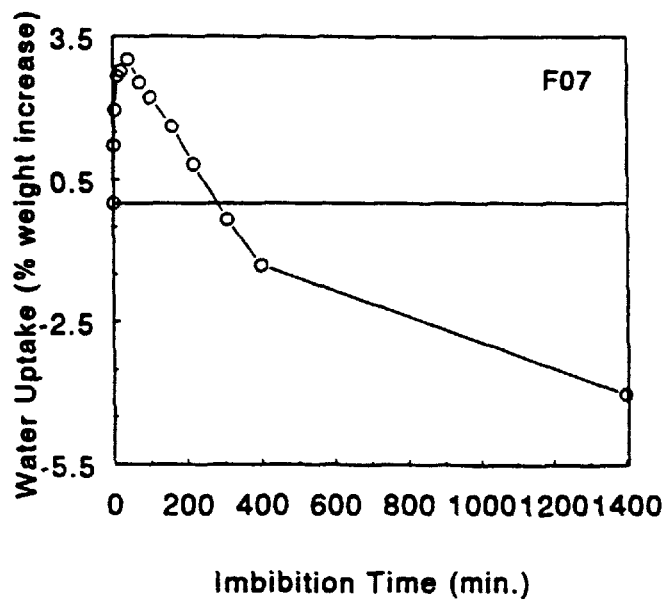
Figure 11:
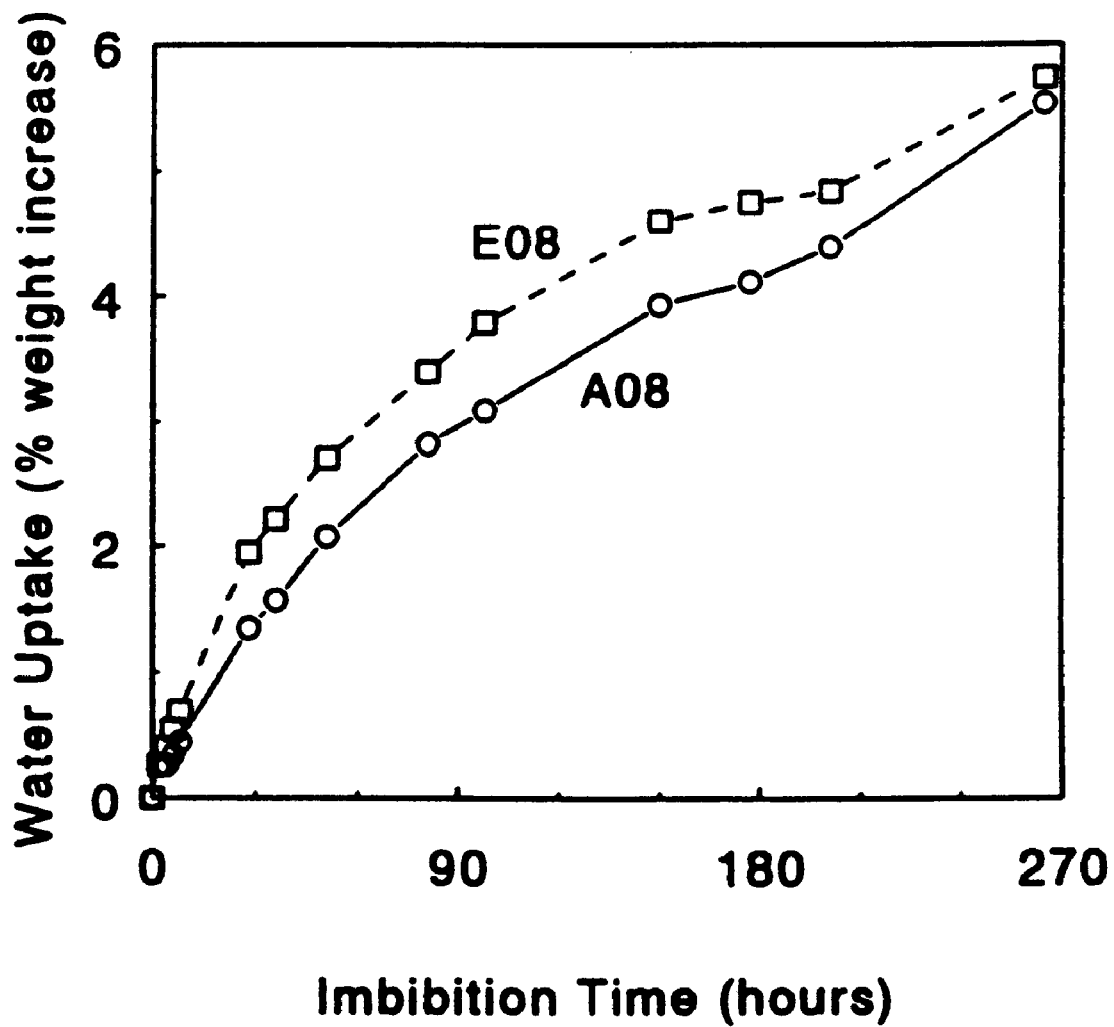
FIG. 11 shows the relationship between water uptake and imbibition time for coatings A08 and E08 as described in the experiments.

We claim:

1. Method for the induction of essentially complete desiccation tolerance in plant embryoids including the steps of treating the embryoids with an amount of abscisic acid activity which is at least about 110% about the amount used to induce quiescence, and coating the embryoids with a mixture of an apolar material and a polar hygroscopic material.

2. Method according to claim 1, comprising a drying step after the treatment with abscisic acid activity.

3. Method according to claim 2, wherein the drying rate of the embryoids is between 0.01 g $H_2O$/g dry weight per hour and 1 g $H_2O$/g dry weight per hour.

4. Method according to claim 1, wherein the embryoids used are in the torpedo stage.

5. Method according to claim 1 whereby the abscisic acid activity is produced at least partly in situ.

6. Method according to claim 5, wherein the abscisic acid activity is induced by stress.

7. Method according to claim 6, whereby the stress is provided through a heat shock.

8. Method according to claim 6, whereby the stress is provided through a low temperature treatment.

9. Method according to claim 6, whereby the stress is osmotic stress.

10. Method according to claim 9, wherein the osmotic stress is provided by a carbohydrate or a polymer.

11. Method according to claim 9, wherein the osmotic stress is provided at a level of –0.5 to –2.5 mPa.

12. Method according to claim 1 wherein exogenous abscisic acid activity is added.

13. Method according to claim 12, wherein the total absisic acid activity is 110–1000% of the activity used to induce quiescence.

14. Method according to claim 12, wherein the exogenous abscisic activity is provided as abscisic acid.

15. Method according to claim 12, wherein the exogenous abscisic acid activity is provided by at least one abscisic acid analog.

16. Method according to claim 1, wherein the treated embryoids are carrot embryoids.

17. Method for germination of embryoids according to claim 16, whereby the embryoids are prehydrated.

18. Method according to claim 17 wherein the prehydration is carried out for 2–8 hours at 100% relative humidity and room temperature.

19. Method according to claim 1, wherein the inorganic material is pumice and the wax-like material is parrafine.

20. Method for the germination of embryoids according to claim 16, whereby the embryoids are imbibed at a temperature of 25–50° C.

21. Method for the germination of embryoids according to claim 16 whereby the embryoids are imbibed in a medium comprising di- or trisaccharides.

22. Method according to claim 16 wherein the abscisic acid activity is present in an amount equivalent to the activity of abscisic acid in the range of 1–100 μM.

* * * * *